Figure 1:
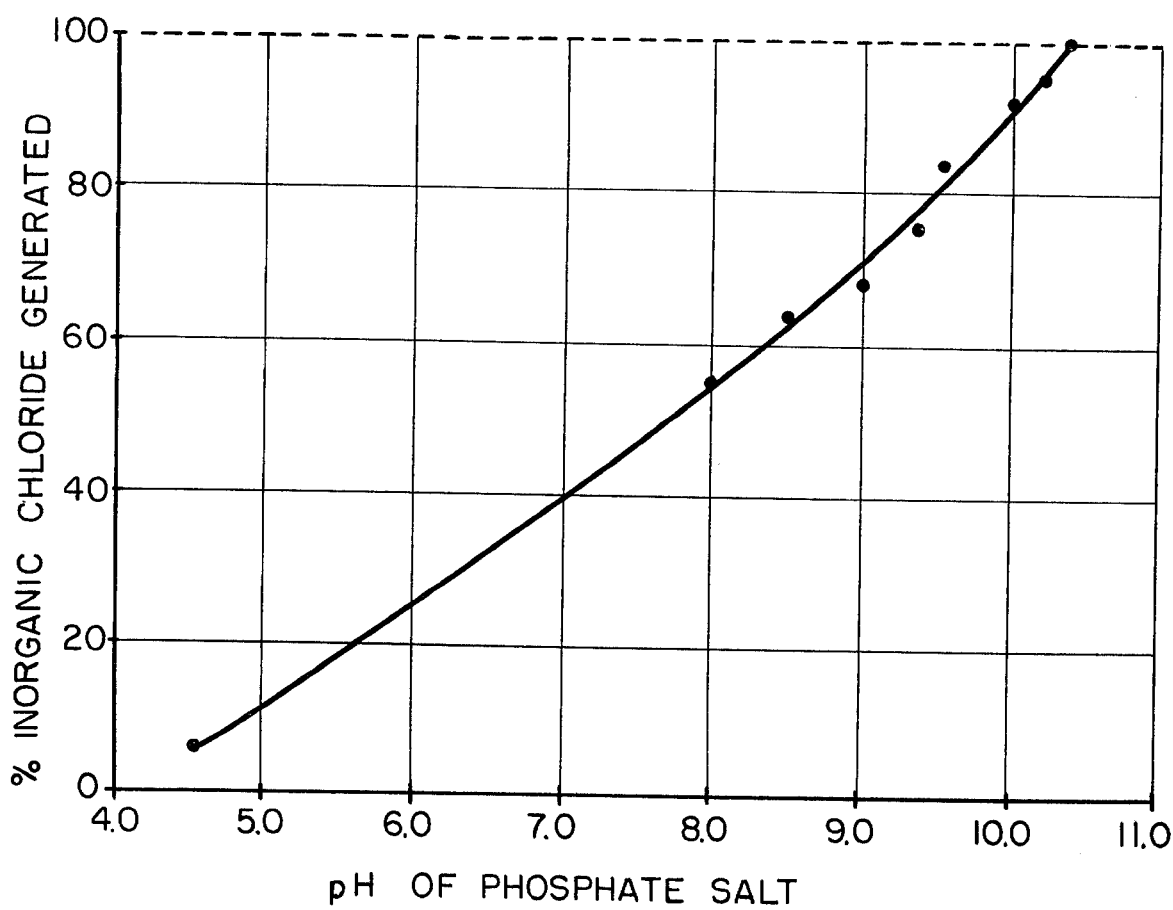

United States Patent [19]

O'Lenick, Jr. et al.

[11] 4,283,542
[45] Aug. 11, 1981

[54] PROCESS FOR THE PREPARATION OF PHOSPHOBETAINES

[75] Inventors: Anthony J. O'Lenick, Jr., Fairlawn; Raymond L. Mayhew, Summit, both of N.J.

[73] Assignee: Mona Industries, Paterson, N.J.

[21] Appl. No.: 965,459

[22] Filed: Nov. 30, 1978

[51] Int. Cl.³ .......................... C07F 9/09; C07F 9/58
[52] U.S. Cl. ................................ 548/112; 260/945; 260/987
[58] Field of Search .............. 260/945, 944, 403, 987; 548/112

[56] References Cited

U.S. PATENT DOCUMENTS

| | | | |
|---|---|---|---|
| 2,980,581 | 4/1961 | Schrader | 260/945 |
| 3,678,137 | 7/1972 | Pfeiffer et al. | 260/944 |
| 3,702,332 | 11/1972 | Pillon et al. | 260/945 |
| 3,799,893 | 3/1974 | Quinlan | 260/944 |
| 4,159,988 | 7/1979 | Eibl et al. | 260/945 |

*Primary Examiner*—Anton H. Sutto
*Attorney, Agent, or Firm*—Sprung, Felfe, Horn, Lynch & Kramer

[57] ABSTRACT

Novel process for the production of phosphobetaine compounds, which process comprises reacting a phosphate ester reactant with an amine reactant, to produce an amphoteric phosphobetaine surfactant having at least one phosphorus-containing anion in the molecule, wherein said phosphate ester reactant is of the formula

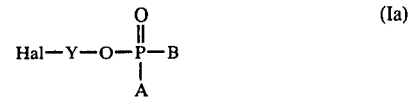

wherein
Hal is halogen
A is selected from $O^-$, OM, and $-O-Y-R^+$
B is selected from $O^-$ and $OM'$
with the proviso that only one of A and B can be $O^-$
Y may be alkylene, optionally interrupted by up to 3 oxygen atoms, of up to 12 carbon atoms, which alkylene chain may optionally be substituted with lower alkyl, alkoxy, hydroxy or hydroxyalkyl, e.g., of not more than 10 carbon atoms each;
$R^+$ represents an amine moiety;
M and M' are individually selected from (a) hydrogen, (b) an organic radical selected from alkyl or hydroxyalkyl of up to 6 carbon atoms, polyhydroxyalkyl of up to 10 carbon atoms, glyceryl, cycloalkyl of up to 6 carbon atoms, aryl or arylalkyl of up to 10 carbon atoms, or (c) a salt radical selected from alkali metals, alkaline earth metals, and mono-, di-, or triethanolamine, with the proviso that when both M and M' are contained in said phosphate reactant and M or M' is an organic radical (b), the other of M and M' must be hydrogen or a salt radical (c).

26 Claims, 3 Drawing Figures

FIG. I.

INORGANIC CHLORIDE GENERATED

| pH | % INORGANIC CHLORIDE |
|---|---|
| 4.6 | 5.5 % |
| 8.0 | 54.0 % |
| 8.5 | 63.0 % |
| 9.0 | 66.2 % |
| 9.4 | 75.0 % |
| 9.5 | 83.6 % |
| 10.0 | 91.0 % |
| 10.2 | 95.0 % |
| 10.3 | 100.0 % |

FOAM PROFILE
0.4% ACTIVE

| pH | FOAM HEIGHT (In Ml) |
|---|---|
| 8.0 | 46 |
| 8.5 | 48 |
| 9.0 | 53 |
| 9.5 | 97 |
| 10.0 | 99 |
| 10.2 | 100 |

SOLUBILITY PROFILE

| pH | CONCENTRATION AT CLOUD |
|---|---|
| 8.0 | 0.95 % |
| 8.5 | 0.78 % |
| 9.0 | 0.52 % |
| 9.4 | 0.29 % |
| 9.5 | 0.12 % |
| 10.0 | 0.12 % |
| 10.2 | 0.12 % |

PROCESS FOR THE PREPARATION OF PHOSPHOBETAINES

BACKGROUND OF THE INVENTION

The present invention relates to novel processes for making certain betaine derivatives referred to hereinafter as "phosphobetaines". More specifically, the invention relates to processes for making amphoteric and switterionic betaine surfactants having at least one phosphorus-containing anion in the molecule.

Betaines and certain substituted betaines are known in the art but the specific phosphobetaines made in accordance with the process of the instant invention have been found to be particularly useful. Thus, the phosphobetaines made by the present invention exhibit outstanding foaming, viscosity-building, wetting, cleansing, detergency, anti-static and emulsifying properties and are therefore useful in industrial applications calling for high performance surface active agents. The compounds are also highly stable species and are extremely well tolerated by human tissue, i.e., they exhibit exceptionally low ocular irritation and oral toxicity, and are therefore eminently suited and useful as surface active agents in personal care compositions.

THE INVENTION

Essentially, the process of the invention comprises reacting a phosphorus-containing reactant, more specifically a phosphate-ester reactant, with an amine reactant, which may be a primary, secondary, or tertiary amine, to produce certain phosphobetaine compounds. In additional aspect, the invention provides certain novel phosphate ester reactants employed in said process and a process for making such phosphate ester reactants in a manner which makes such reactants eminently suitable for conversion into highly efficacious surface active phosphobetaine compounds.

The phosphate ester reactants utilized in the invention can be represented by the formula

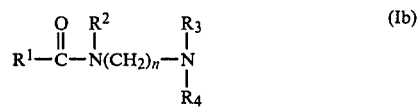

(Ia)

wherein
Hal is halogen
A is selected from $O^-$, OM, and $-O-Y-R^+$
B is selected from $O^-$ and OM'
with the proviso that only one of A and B can be $O^-$
Y may be alkylene, optionally interrupted by up to 3 oxygen atoms, of up to 12 carbon atoms, which alkylene chain may optionally be substituted with lower alkyl, alkoxy, hydroxy or hydroxyalkyl, e.g., of not more than 10 carbon atoms each;
$R^+$ represents an amine moiety, described more fully below
M and M', which may be the same or different, are (a) hydrogen, (b) an organic radical selected from alkyl or hydroxyalkyl of up to 6 carbon atoms, polyhydroxyalkyl of up to 10 carbon atoms, glyceryl, cycloalkyl of up to 6 carbon atoms, aryl or arylalkyl of up to 10 carbon atoms, or (c) a salt radical selected from alkali metals (e.g., sodium or potassium), alkaline earth metals (e.g., magnesium or calcium), and mono-, di-, or triethanolamine. When both M and M' are contained, there is the proviso that when either M or M' is an organic radical (b), the other of M and M' must be hydrogen or a salt radical (c).

As noted above, the amine reactant can be a primary, secondary, or a tertiary amine. Thus, the amine reactants can carry one, two, or three organic radicals, i.e., they can be primary amines having two hydrogens (hereinafter designated R''), secondary amines (hereinafter R'), or tertiary amines (hereinafter R). Preferably, the amine reactant contains not less than 6 or more than 60 carbon atoms total.

The amines employed in the invention contain from one to three organic radicals, i.e., they may contain optionally substituted alkyl, alkenyl, and alkynyl groups, optionally interrupted by hetero atoms, such as oxygen, nitrogen, or sulfur, and can contain other functional groups, e.g., ester or amido moieties, and the amine substituents may, in the case of the secondary and tertiary amines, be themselves linked together to form N-heterocyclic structures, e.g., morpholino. In preferred and more specific embodiments of the invention, the amine reactant is an amidoamine reactant of the formula

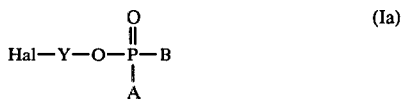

(Ib)

wherein
$R^1$ is alkyl, alkenyl, alkoxy, or hydroxyalkyl of from 5 to 22 carbon atoms each, or aryl or alkaryl of up to 20 carbon atoms,
$R^2$ is hydrogen or alkyl, hydroxyalkyl or alkenyl of up to 6 carbon atoms each or cycloalkyl of up to 6 carbon atoms, preferably of from 2 to 5 carbon atoms, or polyoxyalkalene of up to 10 carbon atoms,
$R^3$ and $R^4$, which may be the same or different, are, in the case of the tertiary amines (R), selected from alkyl, hydroxyalkyl, carboxyalkyl of up to 6 carbon atoms in each alkyl moiety, and polyoxyalkylene of up to 10 carbon atoms; in addition, $R^3$ and $R^4$, taken together with the nitrogen to which they are attached, may represent an N-heterocycle, e.g., a morpholino structure, in which the Y radical is bonded to a ring atom of said N-heterocycle other than the nitrogen of the R moiety; in the case of the secondary amines (R'), one of $R^3$ and $R^4$ is hydrogen, and in the case of the primary amines (R''), both $R^3$ and $R^4$ are hydrogen;
n is an integer from 2 to 12.
(The term "polyoxyalkylene radical" as used above in the definition of $R^2$, $R^3$ and $R^4$ may be of the formula $(R^5-O-R^{5'})_m$ wherein $R^5$ and $R^{5'}$ are alkyl of from 1 to 4 carbon atoms and m is an integer from about 2 to 10).

In different specific and preferred embodiment, the secondary (R') and tertiary (R) amine reactants of the invention may be an N-heterocyclic radical which may contain one additional hetero atom (e.g., oxygen or another nitrogen) and contains 5 to 6 total ring carbon atoms; optionally, said heterocyclic radical may be substituted with alkyl and/or hydroxyalkyl of up to 20 carbon atoms each. Typical of such N-heterocyclic radical are imidazolyl, N-alkylmorpholino, alkylpyrimidino, alkoxazolinyl, and the like. The substituents in formula I(c) are as follows:

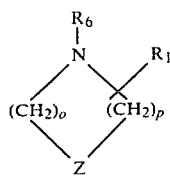
(Ic)

wherein
- Z is N or O;
- o is an integer from 0 to 3;
- p is an integer from 1 to 3 provided that the sum of o+p is from 3 to 4;
- $R^1$ is defined as before and is linked to a ring carbon atom; and
- $R_6$ is, in the case of the tertiary amines (R), alkyl of from 2 to 6 carbon atoms which may be substituted with a hydroxyl group at the terminal or a non-terminal carbon atom, in the case of the secondary amines (R'), $R_6$ is hydrogen.

The process of the invention is explained below with specific reference to the tertiary, secondary, and primary amine variants.

TERTIARY AMINE REACTANTS

When using a tertiary amine reactant for reaction with the phosphate-ester reactant, the process of the invention may be represented by the following generic reaction scheme (1):

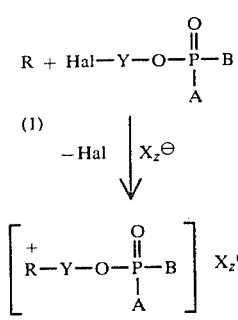
(Ia)

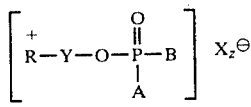
(I)

wherein
- R is a tertiary amine, i.e., carrying three organic radicals, preferably containing a total of from 6 to 60 carbon atoms;
- $X^-$ is an anion; and
- z is an integer from 0 to 2 and z is of a value necessary for charge balance (i.e., when A and B are $O^-$ and OM', or OM and $O^-$, respectively, z is 0; when A and B are OM and OM', or $-O-Y-R^+$ and $O^-$, respectively, z is 1; when A is $-O-Y-R^+$ and B is OM', z is 2);

When A in formula I(a) is $-O-Y-R^+$, two moles of R are required per mole of phosphate ester reactant (Ia).

Still more specific sub-embodiments of reaction scheme (1), i.e., in which particular phosphate ester reactants are employed, can be represented as follows:

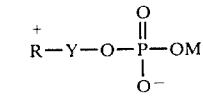
(II)

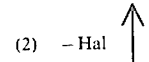

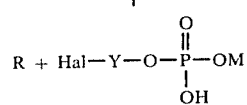
(IIa)

wherein Hal = halogen and the other radicals are defined as above

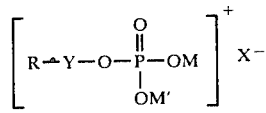
(III)

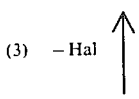

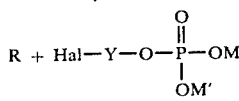
(IIIa)

wherein the radical are defined as above; and

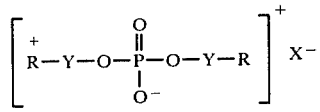
(IV)

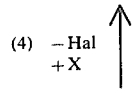

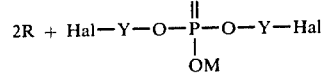
(IVa)

wherein the radicals are defined as above.

SECONDARY AMINE REACTANTS

When using a secondary amine reactant with the phosphate-ester reactant, the process of the invention may be represented by the following generic reaction scheme:

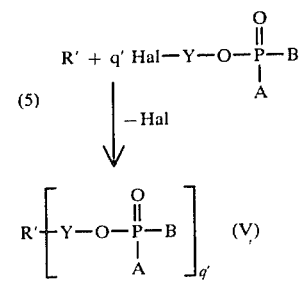
(V)

wherein

R' is a secondary amine, i.e., carrying two organic radicals, preferably of a total of 6 to 40 carbon atoms, and q' represents the moles of phosphate-ester reactant used which can be 1 or 2, or higher.

It will be understood that when one mole of phosphate ester reactant is employed per mole of secondary amine reactant R' (i.e., when q'=1), the reaction proceeds as follows:

(6)
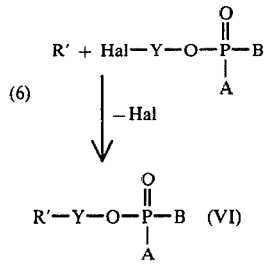

wherein the radicals are defined as above.

When two moles of the secondary amine reactant are supplied (i.e., when q'=2), the reaction leads to a bis-compound, as follows:

(7)
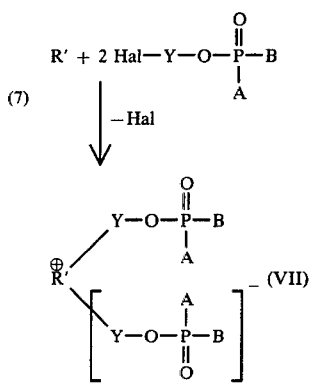

wherein
the radicals are defined as above,
and one of the A or B radicals is O⁻ as shown, for charge balance.

The secondary amine reactant R' can, in preferred and specific aspect, be of the formula I(b) given supra, provided, however, that R₃ therein is hydrogen, to give the secondary amine function. Also, R' can be a cyclic amine reactant of the formula I(c) given supra, with the proviso that R₆ therein is hydrogen, to give the secondary amine function.

PRIMARY AMINE REACTANTS

When using a primary amine reactant with the phosphate ester reactant, the process of the invention may be represented by the following generic reaction scheme:

(8)
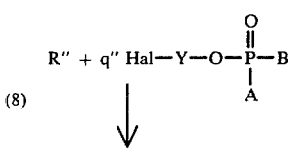

-continued

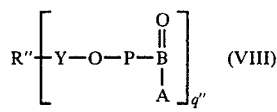

wherein
R" is a primary amine, i.e., carrying one organic radical, preferably of a total of 6 to 20 carbon atoms, and q" represents the moles of phosphate-ester reactant used which can be 1, 2, 3, or higher.

It will be understood that when one mole of phosphate ester reactant is employed per mole of primary amine reactant R" (i.e., when q"=1), the reaction proceeds as follows:

(9)
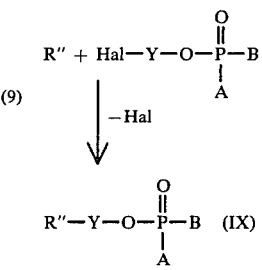

wherein the radicals are defined as above.

When two moles of the primary amine reactant are supplied per mol of phosphate ester reactant, i.e., when q is 2, the reaction leads to a bis compound, as follows:

(10)
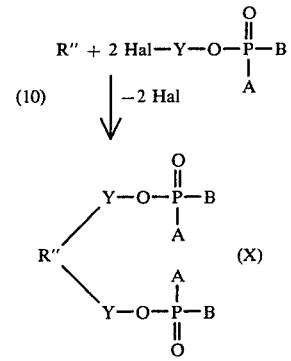

wherein the radicals are defined as before.

When three moles of the primary amine reactant are supplied, i.e., when q is 3, the reaction leads to a tris-compound, as follows:

(11)
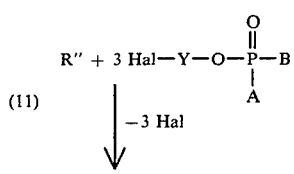

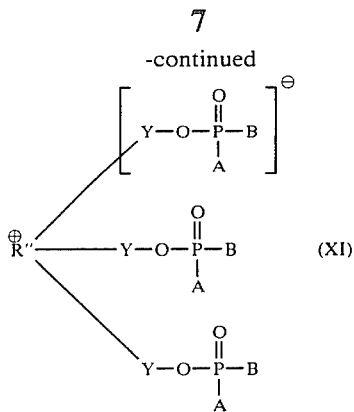

wherein
the radicals are defined as before,
and one of the A or B radicals is O⁻ as shown, for charge balance.

The primary amine reactant R″ can, in preferred and specific aspect, be of the formula I(b) given above, provided, however, that $R_3$ and $R_4$ therein are hydrogen, to give the primary amine function.

An alternative process for making certain of the phosphobetaine compounds utilizes a novel reaction between the amine reactant and a cyclic hydroxypropylene-containing phosphate ester reactant, to produce 3-hydroxypropylphosphobetaines, as shown schematically below for a tertiary amine reactant:

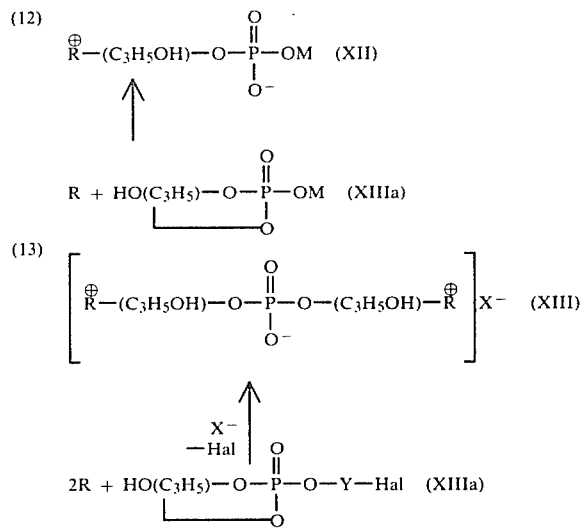

wherein the reactants are defined as before, it being understood that the anion X⁻ can be supplied by the halide (Hal) group which is split from reactant IVa or VIa (in which case X⁻ = Hal) or from another source, as explained above. The designations "HO(C₃H₅)" or "(C₃H₅OH)" herein refer to a hydroxypropylene function in which the hydroxy can be linked to any one of the three carbons and the cyclic oxa-moiety is linked to one of the three carbons, either at the 3- or 2-position of the propyl group.

The reactions proceed in the same manner using primary amines (R″) or secondary amines (R′), instead of the tertiary amine (R) shown, it being understood that use of secondary amines can give bis-compounds as in Reaction (7), supra, and use of primary amines can give bis- or tris-compounds, as shown in Reactions (10) and (11), supra, when the cyclic phosphate reactant is supplied in appropriate multiple molar ratio (2:1 or 3:1, respectively).

The reactants required in the processes can be prepared as follows.

PREPARATION OF INTERMEDIATE AMINE REACTANTS

The amine reactants R, R′, and R″ are known or are generally prepared in accordance with conventional techniques. For instance, when making a tertiary amine (R) of the amidoamine type (Ib), this can be prepared by reacting an acid with an aminoalkyl-substituted tertiary (or secondary or primary, in the case of R′ and R″) amine to result in the amidoamine function. Alternatively, an acid can be reacted with an aminoalkyl-substituted secondary or primary amine, followed by further treatment of the reaction product with alkylene oxide, to give the tertiary or secondary reactants, respectively. When R or R′ is the N-heterocyclic structure (Ic), e.g., imidazolyl, this can be prepared in accordance with known techniques, e.g., as taught in U.S. Pat. No. 2,267,965.

Reaction (14) below yields the non-cyclic reactants "R" and Reaction (15) illustrates the preparation of a typical cyclic amine reactant R (Imidazolyl):

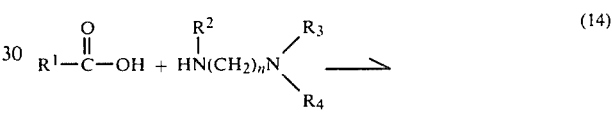

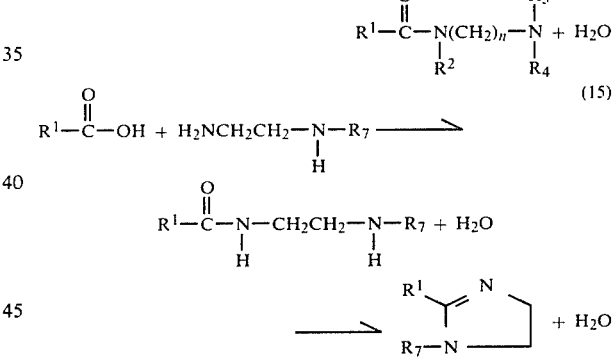

wherein $R^1$ is defined as above and $R^7$ is alkyl of 2 to 6 carbon atoms which may be substituted with a hydroxyl group (at the terminal or a non-terminal carbon atom). This cyclic reactant can be prepared as disclosed in U.S. Pat. No. 2,267,965.

A wide variety of commercially available amines are suitable for these reactions. The amines can be primary, secondary or tertiary with only the proviso that the total number of carbons be greater than 6, i.e., to give a hydrophobe necessary for surface active properties. All other substitutions and modifications of the amine are usable in the present process. Of the commercially available aliphatic amines, there may be mentioned "Armeen" (Armak Chemical), e.g., octyl amine through dodecyl amine. Illustrative aliphatic secondary amines of similar molecular weight include such secondary amines as the "Armeen 2C" (dicocamine) through the disoya amine, tallow amine. Tertiary amines may be simple aliphatic tertiary amines such as the type alkyl dimethyl amine, dialkyl methyl amine, and trialkyl amine, marketed by Armak Chemical Company and an example is "Armeen DM14D" (which is the N-tetradecyl dimethyl amine). Further, ethoxylated aliphatic amines can also be used. These products are marketed under the names of "Ethameen". Any substitution is possible as illustrated elsewhere herein.

PREPARATION OF PHOSPHATE ESTER INTERMEDIATE REACTANTS

The preparation of the phosphate ester intermediate reactants (Ia), (IIa), (IVa), (Va) and (VIa) set forth in the reaction sequences above are also prepared by reactions which are illustrated as follows:

(16) 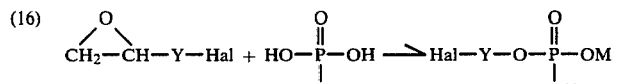

(17) 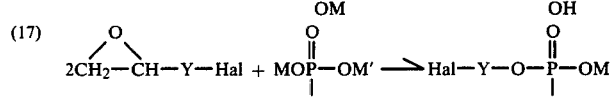

(18) 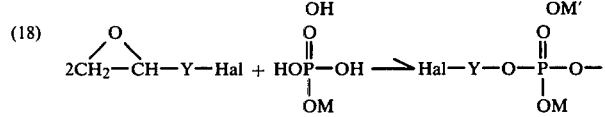

For certain reactants IIa, viz., those wherein M is hydrogen or an alkali or alkaline earth metal cation, the following intermediate synthesis can be used:

(19) 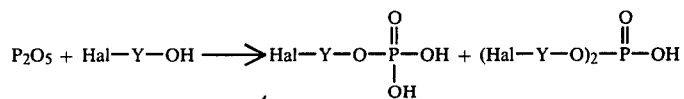

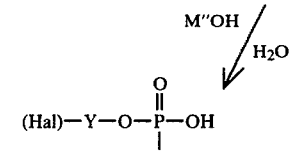 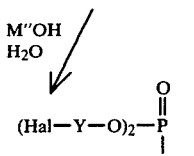

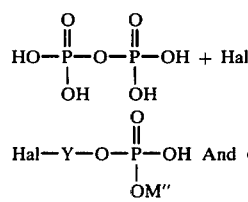 (20)

wherein
  M" is an alkali or alkaline earth metal salt cation (e.g., sodium, potassium, magnesium or calcium)

Reactions (19) and (20) are carried out in two steps. The first is conducted under anhydrous conditions to generate α-chloro phosphate. Subsequently, this material is diluted to 40% with water and one mole equivalent of M"OH, e.g., sodium hydroxide.

The cyclic phosphate ester intermediate reactants required for the alternative synthesis routes (12) and (13) supra, can be prepared as follows:

(21) 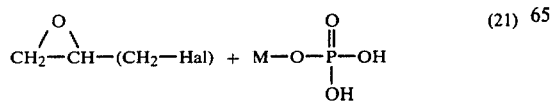

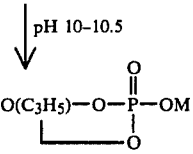 (Va)

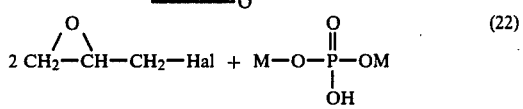 (22)

 (VIa)

(IIa) 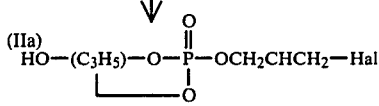 (IIIa)

(IVa)

It will be noted that Reactions (21) and (22) utilize reactants similar to the reactants needed in Reactions (17) and (18) supra (although with the more limited hydroxypropyl definition), but that different, cyclic, products are obtained. The different products are the result of a different pH adjustment; thus, while reaction (17) is carried out at a pH of about 4–5, reaction 18 is carried out at a pH of 9.5 to 10.5, resulting in a cyclic product. This cyclic product may contain also some vicinal epoxy material so that the formula

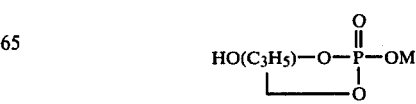

should be understood as including not only one or more of the isomers resulting from linkage of the oxa-oxygen to any one of the hydroxy-propylene carbons (to make a 5-, or 6-membered ring), but also the following structure:

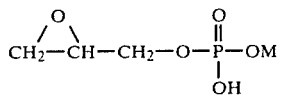

Operation at a higher pH, e.g., 10.5 or higher, favors formation of the vicinal epoxy-containing material.

The reaction of epichlorohydrin with phosphoric acid and various phosphate salts has not been investigated to an appreciable extent and very little has been written in the literature on this reaction. We have observed that a variety of products can be obtained with variation of certain experimental parameters. The most important of these parameters include the pH of the phosphate salt, the mole ratio of the phosphate salt to the epichlorohydrin and the temperature at which the reaction is run. Reactions No. 16 through 18 occur in an acidic, aqueous solution. Consequently, the reaction proceeds by attack at the epoxide resulting in a 3-chloro-2-hydroxypropyl phosphate intermediate. This intermediate, containing a labile organic chlorine, is reacted with certain nucleophilic species such as amine to give the product conforming to the general phosphobetaine structure. The pH at which this reaction occurs must be strictly controlled. The desired pH range is from 4 to 5. If the pH drops below 4 there is significant hydrolysis of the phosphate ester. If the pH at which the reaction is run is too high, there will be loss of labile organic chlorine. When the reaction is carried out in an alkaline environment of a pH 9.5–10.5 optimally, the resulting intermediate had surprisingly lost its labile organic chlorine and formed a cyclic diester. This diester is quite resistant to hydrolysis but extremely reactive towards certain nucleophilic species. This nucleophilic attack, particularly under conditions at which it is maximized, coupled with the proper selection of amine having a hydrophobic nature makes this process of the invention a commercially viable procedure for preparing surface active agents possessing unusual and valuable properties.

The following conditions represent preferred operating conditions:

(1) The reaction should be carried out in an aqueous environment at a concentration of the reactants of 30–50% based on total solution (the balance being water); most preferably the reactants constitute about 40% of the total reactant/water mixture.

(2) The phosphate salt used should have the pH of 9.5–10.5 before the addition of epichlorohydrin. This will allow for maximum formation of the cyclic phosphate diester.

(3) The reaction is preferably initially conducted at a temperature of 80°–85° C. under some pressure, e.g., 5 psig of nitrogen, to prevent azeotrope reflux. The temperature is gradually increased to 100° C. and held until theoretical inorganic chloride is generated.

The reaction of epichlorohydrin with disodium and trisodium phosphate has been described or reported in the literature; O. Bailly, Compt. Rend. 172, 689–91 (1921); C.A. 15, 1884 (1921) and O. Bailly, Bull. Soc. Chim. (4) 31, 848–62 (1922); C.A. 17, 264 (1923). In the reported reaction of disodium hydrogen phosphates with epichlorohydrin a diglycerophosphoric acid diester was thought to have been obtained. As noted above, however, we have found that the pH of this system has a profound effect on the product which is obtained. For example, by reacting $NaH_2PO_4$ with epichlorohydrin, the following two products can be obtained, depending on the mole ratio of the two reactants.

If one mole of epichlorohydrin is reacted, the product is 3-chloro-2-hydroxypropyl phosphate (Intermediate Reactant A, below). If two moles are reacted, there is obtained bis(3-chloro-2-hydroxypropyl phosphate); Intermediate Reactant "D", below. These reactions are carried out at a pH of 4–5. Under these conditions, as can be seen from the products obtained, the phosphoric acid moiety attacks the epoxy ring. As the pH is increased to form disodium phosphate, a nucleophilic attack occurs with a displacement of significant quantities of chloride ions.

This is shown in the appended drawing, in which

FIG. 1 is a plot showing the effect of pH on chloride generation.

At a pH of 9.5–10.5, theoretical chloride generation is achieved. Although it was assumed that simultaneous attack was occurring at the epoxy moiety, it was surprisingly discovered that the epoxide group was being retained essentially intact. The product obtained under these conditions was 2,3-epoxymonosodium propyl phosphate (Intermediate Reactant "C", below). The presence of the epoxy group was subsequently verified by reaction with various amine compounds.

Figure 2:
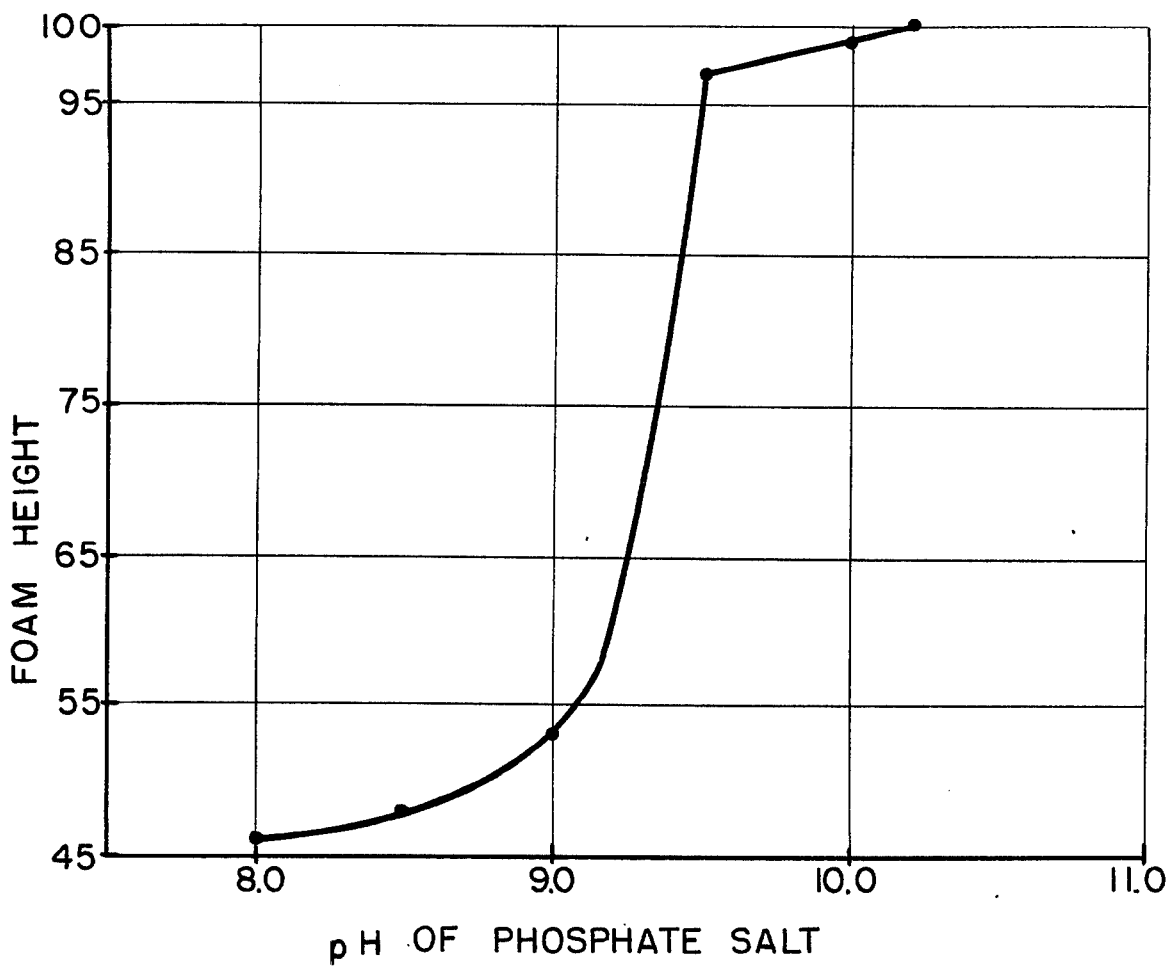

The various intermediates were used to react with various primary, secondary and tertiary amines to form the ultimate amphoteric phosphobetaine compounds. Although similar product would be expected to be obtained when utilizing Intermediate Reactants A and C, distinctly different properties were found for products prepared from these two intermediates. In the case of Intermediate Reactant C, significantly higher foaming products were obtained and this was later shown to be a function of pH of the initial phosphate salt used; this effect is depicted in the drawing wherein FIG. 2 is a graph captioned "Foam Profile", which is a plot of foam height versus the pH of the initial phosphate salt used.

Figure 3:
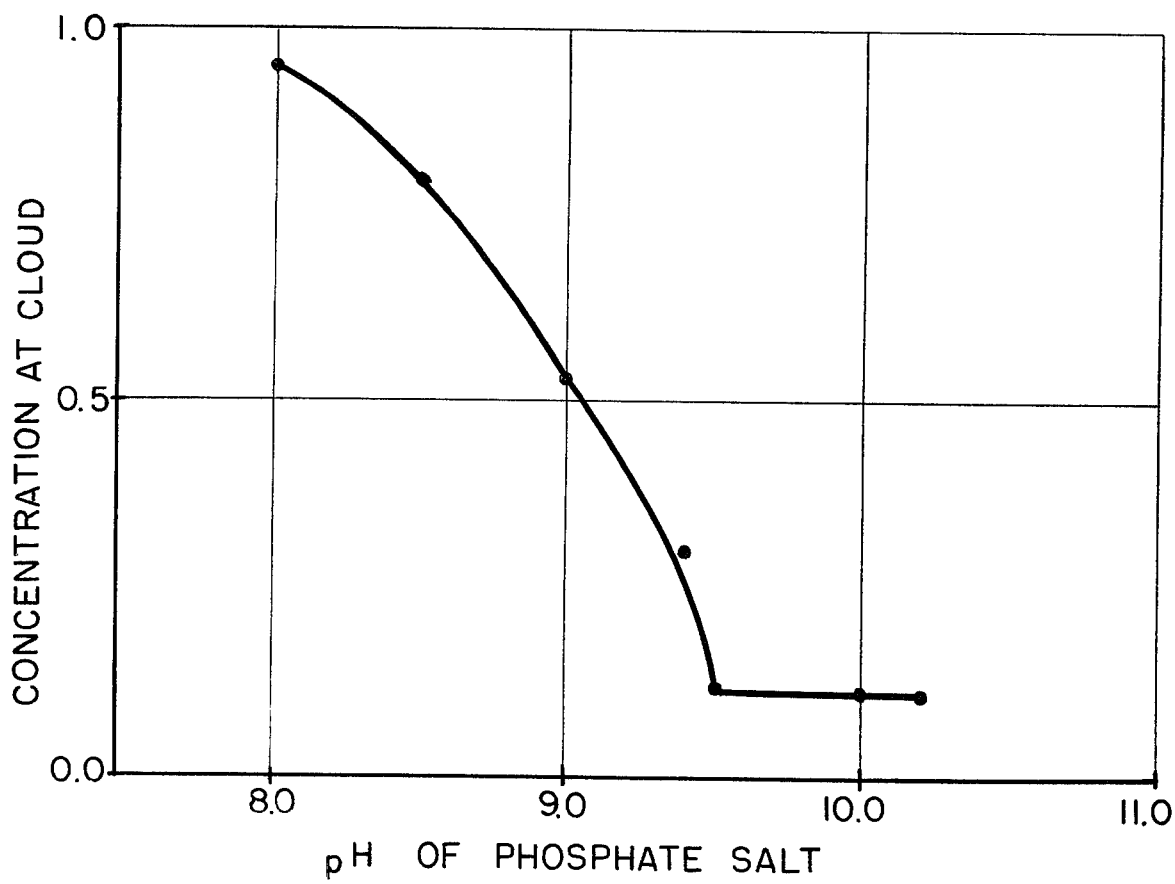

One of the interesting phenomenon of these products is thus their pH dependent solubility. Not only are the products pH-dependent, but they are also concentration-dependent in that very dilute concentrations tend to become cloudy. The concentration at which this clouding phenomenon occurs is affected by the pH of the initial phosphate salt. This is shown in the appended drawing wherein FIG. 3 is a plot of pH versus concentration at which cloudiness occurs.

At a pH of 9.5–10.5, there is a leveling off of the solubility.

As noted above, the process parameters must be controlled in order to maintain the reactive organic chlorine atom in the phosphate ester reactants and to avoid hydrolysis of these phosphate esters. Thus, the pH of the phosphate salt employed, the temperature of the reaction and the reaction time were all found to be important in yielding the desired intermediate product. The nature of the intermediate product in turn has a profound effect on the properties of the final phosphobetaine products.

Indeed, the surprising reactivity of the cyclic phosphate ester intermediate reactants, like that of their labile chlorine containing analogues, while at the same time their stability against hydrolysis renders eminently suitable for use in the basic process of the invention to yield the ultimate phosphobetaine materials. When amine reactants are employed, which are sufficiently hydrophobic to surface-active, highly efficacious surface-active phosphobetaines are produced. However, non-surface-active analogues can also be prepared by using low molecular weight of hydrophilic amines.

With respect to reactions 19 and 20 supra, wherein various halogen-containing alcohols are reacted with phosphorous pentoxide or polyphosphonic acid, the mixture of products formed as shown in those reaction sequences is preferably diluted in water (after the first step is conducted under anhydrous conditions to generate the α-chlorophosphate as set forth above), preferably to a concentration of about 40% of second step reactants in the aqueous mixture, and a suitable base, e.g., 1 mol equivalent of sodium hydroxide, is added to adjust the pH to approximately 5 to 6. It should, of course, be understood that these intermediate reactions 19 and 20 permit preparation of many phosphate ester reactants, not only 2-hydroxypropyl phosphate halogen types as illustrated by reactions 16 to 18, but compounds of the latter type can also be made so that this represents an alternate synthesis. However, it is a feature of that aspect of the process of the invention which utilizes the aforesaid cyclic intermediates, (i.e., as illustrated in reactions 16 to 18) that the ultimate phosphobetaine products produced have different properties depending on which intermediate was utilized. In the case of reactant C for instance, i.e., where a cyclic phosphate ester is utilized, significantly higher foaming ultimate phosphobetaine products were obtained. Accordingly, use of these cyclic intermediates is a preferred aspect of the invention.

Specific phosphate ester intermediate reactants which were prepared according to reaction sequences 16–22 supra and which were used in the examples, infra, in conjunction with certain tertiary amine reactants, are set forth below:

PHOSPHATE ESTER INTERMEDIATE REACTANTS

Reactant "A"-Prepared According to Reaction Sequence 16

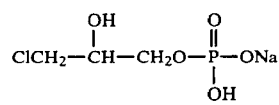

Reactant "C"-Prepared According to Reaction Sequence 17

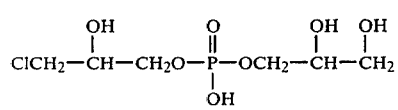

Reactant "C"-Prepared According to Reaction Sequence 21

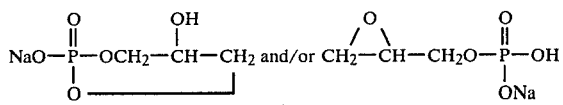

Reactant "D"-Prepared According to Reaction Sequence 18

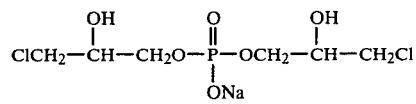

Reactant "E"-Prepared According to Reaction Sequences 20

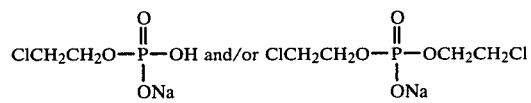

Reactant H. Prepared According to Reaction Sequence 19

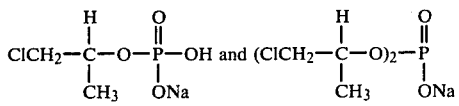

Reactant F. Prepared According to Reaction Sequence 20

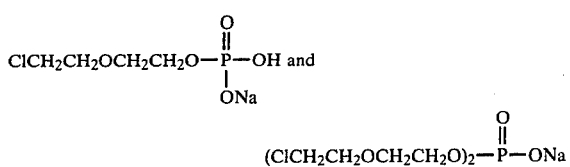

Reactant G. Prepared According to Reaction Sequence 20

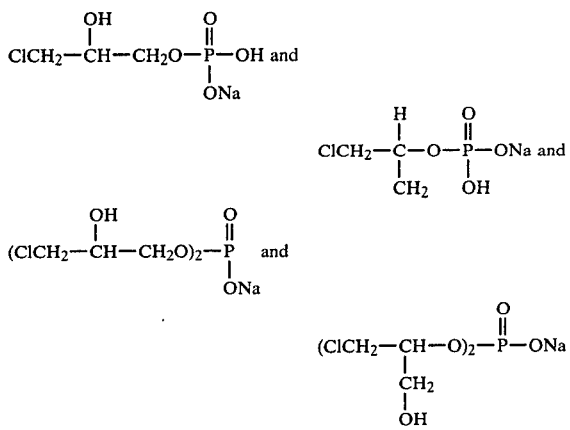

Reactant "I"-Prepared According to Reaction Sequence 20

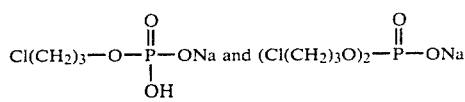

In carrying out the reactions 1 to 13 as set forth above leading to the ultimate phosphobetaine compound of the invention, the amine intermediate reactant (R, R', or R"), is reacted with the appropriate phosphate ester intermediate reactant and these reactions are generally carried out in an aqueous system at 80°–100° C.

The optimum concentration range of the reactants in reactions 1 to 13 in aqueous solution is from 30–50% and most preferably the reactants constitute about 40% of the aqueous reactant mixture. In this respect, the preferred concentration are similar to those set forth above for certain intermediate reactions, e.g., in the preparation of the cyclic intermediates according to reactions 16 to 18 the resulting reactions product mixture, which preferably will contain about 40% of active reactants, may be used as such in carrying out the final reaction leading to the ultimate phosphobetaine.

The phosphate ester reactant should have a pH of about 5 to 6 before the amine addition and the pH should be maintained at between 7 to 9 after said amine addition; below a pH of 7 the rate of quaternization slows significantly and, of course, the pH of the amines used themselves limit the pH on the alkaline topside at about pH 9.

As noted above, the reactions 1 to 13 are generally carried out at a temperature of about 80°–100° C. The reaction is preferably initially conducted at a temperature of 80°–100° C. and may be conducted under some pressure, e.g., under 5 psig of nitrogen. However, under pressure, higher temperatures can be used, e.g., temperatures up to about 130° C. and the ceiling temperature is determined by the sensitivity of the reactants, e.g., the amine reactant, since it will be found that color loss and evidence of other degradation occurs at unduly high temperatures.

Many specific examples of ultimate phosphobetaine preparation are set forth below.

The ultimate phosphobetaines are good surfactants and quite unexpectedly exhibit good foam volume and superior foam stability in comparison to commercially available amphoteric and zwitterionic surfactants. This was determined by an adaptation of the well known Ross-Miles foam test principle ["Oil and Soap" 18, 99–102 (1941)] in the following manner.

Lanolin, anhydrous, cosmetic grade is mixed with dioxane (technical grade) in the proportion of 2.5 grams lanolin and 100 grams of dioxane. The lanolin is first mixed with 25 cc of dioxane. This mixture is heated over a steam bath to 45° C. in order to dissolve the lanolin in the dioxane. The remainder of the dioxane is then added and mixed. This lanolin-dioxane solution, which is stored in an amber bottle, should be prepared fresh on the day that the tests are run.

The composition to be tested is diluted by adding 376 cc of distilled water to 4 grams of the composition and then by adding 20 cc of the lanolin-dioxane solution described above while mixing. Heat is produced when the lanolin-dioxane solution is added to the solution of the composition in water and care must be taken in adjusting the temperature of this solution to 24°–25° C.

Both of these intermediate solutions should therefore be adjusted to 23° C. before mixing. The cooling of the lanolin-dioxane solution should be gradual in order to avoid precipitation of the lanolin. This will produce a final solution with a temperature of 24°–25° C.

The final solution of the composition to be tested, water, dioxane and lanolin described above, is then run in a modified Ross-Miles foam column in the usual way. All tests are conducted in duplicate, and the average of the two results is taken. Foam stability is determined by measuring the decay in foam height after two minutes, expressed as a percentage of the original height.

Typical foam values obtained utilizing the above procedure for an alkylamidophosphobetaine, an alkylamido betaine and an alkylamido sultaine are listed below:

| | Example No. | Foam Volume (ml) | % Decay After 2 min. |
|---|---|---|---|
| Lauric Myristic Amido 3-Hydroxypropyl Phosphobetaine | 10 | 250 | 4.0 |
| Cocamido Disodium 3-Hydroxypropyl Phosphobetaine | 9 | 240 | 10 |
| Cocamido Disodium Ethyl Phosphobetaine | 47 | 210 | 19 |
| Cocamido Propylbetaine | — | 225 | 31.0 |
| Cocamido Propylsultaine | — | 200 | 60.0 |

As can be seen from the above results, the phosphobetaines made by the process of the invention exhibit excellent foam volume and stability, whereas the stability of the betaines and sultaines is significantly less.

In another series of tests, additional species of the phosphobetaine compounds of the invention were tested by a "cylinder shake test" for the evaluation of foaming characteristics.

In this test, test solutions containing 0.1% by weight of the candidate surfactant in water of 100 ppm hardness (calcium to magnesium ration 3:2) were used and placed in 100 ml stoppered cylinders which had been cleaned so that water drains down its walls in an unbroken film. Each cylinder filled with test solution was shaken 20 times in a standard manner and net foam in ml is noted one minute and again five minutes after shaking. The test were run in three replicates. The results were as follows:

| Lauric/Myristic Type | Example Number | 1 Minute | 5 Minutes |
|---|---|---|---|
| Lauric Myristic Amido Betaine | — | 67 | 60 |
| Sodium Lauryl Sulfate | — | 85 | 74 |
| Lauric Myristic Amido Monosodium Phosphobetaine | 2 | 88 | 78 |
| Lauric Myristic Amido Disodium Phosphobetaine | 10 | 85 | 78 |
| Lauric Myristic Amido Glyceryl Phosphobetaine | 2 | 86 | 78 |
| Lauric Myristic Amido Carboxy Disodium Phosphobetaine | 62 | 87 | 73 |
| N-cocamidoethyl-N-hydroxyethyl glycine | — | 76 | 67 |
| Coco Type | Example Number | 1 Minute | 5 Minutes |
| Cocobetaine | — | 65 | 56 |
| Cocamidobetaine | — | 70 | 63 |

| | -continued | | |
|---|---|---|---|
| Cocoamido Monosodium Phosphobetaine | 1 | 79 | 74 |
| Cocamido Glyceryl Phosphobetaine | 20 | 71 | 74 |
| Coco Imidazoyl Monosodium Phosphobetaine | 37 | 83 | 78 |
| Coco Imidazoyl Disodium Phosphobetaine | 49 | 80 | 75 |
| Bis(Coco Imidazoyl) Phosphobetaine | 63 | 75 | 69 |

In addition, the compounds of the present invention possess a surprisingly low ocular irritation potential when compared to commercially available amphoteric and zwitterionic surfactants. The test employed is the modified Draize Test (J. H. Draize et al, Toilet Goods Assn. No. 17, May, 1952, No. 1 Proc.Sci.Sect.).

In this method, a 0.1 ml sample of a neutral solution of the compound under investigation is dropped into one eye of an albino rabbit, the other eye serving as a control. Six rabbits are employed for each compound.

Observations are made after 1, 24, 48, 72 and 96 hours and 7 days after initial instillation; second and third instillations are made after the 24 and 48 hour readings. Results may vary from substantially no change, or only a slight irritation in the appearance of the rabbit's eye after 7 days, to severe irritation and/or complete corneal opacity. Ocular lesions are scored for the cornea, iris and conjunctiva with a higher number indicating greater ocular irritation and the scores are added to give a total numerical value for each reading for 6 rabbits and average. The averaged score is an indication of the irritation potential of the composition under test. Based on the averaged score, descriptive irritation evaluation may be given, e.g., none, slight, moderate, severe, etc.

Typical results for a betaine, sultaine and a phosphobetaine in accordance with the present invention when subjected to the above test procedure are as follows:

| Compound | Eye Irritation Potential | | | | | | Irritant Rating |
|---|---|---|---|---|---|---|---|
| | 1 hr. | 24 hr. | 24 hr. | 72 hr. | 96 hr. | Day 7 | |
| Lauric Myristic Amido 3-Hydroxypropyl Phosphobetaine | 7.7 | 0.3 | 1.3 | 1.0 | 0.0 | — | slight |
| Cocamido Propylbetaine | 11.7 | 4.2 | 9.3 | 13.2 | 11.2 | 5.8 | severe |

| Compound | Eye Irritation Potential | | | | | | Irritant Rating |
|---|---|---|---|---|---|---|---|
| | 1 hr. | 24 hr. | 24 hr. | 72 hr. | 96 hr. | Day 7 | |
| Propylsultaine | 15.0 | 8.5 | 15.6 | 25.0 | — | — | severe |

All tests were conducted at a concentration of 3% wt/wt.

In further series of tests carried out as above, but using only one test rabbit per compound, the following results were obtained:

| | Example Number | Day | | | | | Irritant Rating |
|---|---|---|---|---|---|---|---|
| | | 1 | 2 | 3 | 4 | 7 | |
| Lauric Myristic Disodium Amido Phosphobetaine | 10 | 7 | 0 | 1 | 1 | 0 | very slight |
| Glyceryl "CA-35" | 33 | 4 | 0 | 0 | 0 | 0 | very slight |
| Lauric Myristic Carboxy Disodium Phosphobetaine | 62 | 2 | 2 | 0 | 0 | 0 | very slight |
| Comparison | | | | | | | |
| Amphoteric 20* | — | 21 | 15 | 7 | 5 | 0 | moderate |
| Lauric Myristic Amido Betaine | — | 8 | 15 | 25 | — | — | severe |
| Cocobetaine | — | 23 | 26 | 19 | 17 | 25 | severe |
| Cocamidobetaine | — | 21 | 19 | 14 | 9 | 6 | severe |
| Sodium Lauryl Sulfate | — | 18 | 16 | 16 | 16 | 10 | severe |
| CA-35** | — | 26 | 21 | 21 | 16 | 0 | severe |

*N-cocamidoethyl-N-hydroxyethyl glycine
**2-undecyl-1-hydroxyethyl propionic acid imidazoline As can be readily seen, the phosphobetaines in accordance with the present invention exhibit only slight ocular irritation, whereas the betaines and sultaines are severe irritants.

The following examples illustrate the process of the invention and the novel intermediates utilized therein.

EXAMPLE 1

20.5 parts of Reactant "A" and 60.0 parts of water are charged in a reacting vessel under good agitation. Heat is applied to 50° C. 19.5 parts of molten 3-cocoamidopropyl dimethylamine are slowly charged under good agitation. Heating is continued to 90°–95° C. and held at this temperature for 3 to 4 hours. Reaction reaches 97% during this time via inorganic chloride and tertiary amine analysis.

The product is an aqueous solution of a novel product having the following structure:

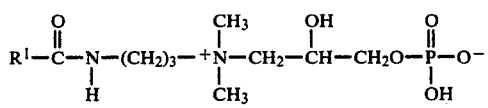

$R^1 = C_7$ to $C_{17}$ alkyl

EXAMPLE 2

20.8 parts of Reactant "A" and 60.0 parts of water are charged in a reacting vessel under good agitation. Heat is applied to approximately 50° C. 19.2 parts of a 70/30 blend of lauramidopropyl dimethylamine and myristamidopropyl dimethylamine are slowly charged to the above solution using good agitation. Heating is continued to 90°–95° C. and held at this temperature for 3 to 4 hours. Reaction reached 97% during this time via inorganic chloride and tertiary amine analysis.

The product is an aqueous solution of a novel product having the following structure:

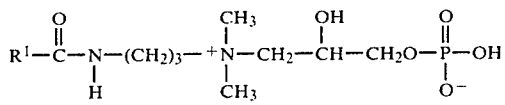

R¹ = 70% C₁₁ alkyl
30% C₁₃ alkyl

EXAMPLE 3

23.2 parts of Reactant "A" and 60.0 parts of water are charged in a reacting vessel under good agitation. Heat is applied to approximately 50° C. 16.8 parts of 3-lauramidopropyl dimethylamine are slowly charged to the above solution using good agitation. Heating is continued to 90°–95° C. and held at this temperature for 3 to 4 hours. Reaction reached 97% during this time via inorganic chloride and tertiary amine analysis.

The product is an aqueous solution of a novel product having the following structure:

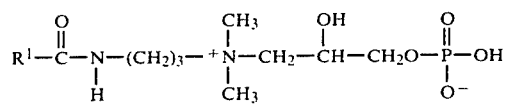

R¹ = C₁₁ alkyl

EXAMPLE 4

23.9 parts of Reactant "A" and 60.0 parts of water are charged in a reacting vessel under good agitation. Heat is applied to approximately 50° C. 16.1 parts of caprylamidopropyl dimethylamine are slowly charged to the above solution using good agitation. Heating is continued to 90°–95° C. and held at this temperature for 3 to 4 hours. Reaction reaches 97% during this time via inorganic chloride and tertiary amine analysis.

The product is an aqueous solution of a novel product having the following structure:

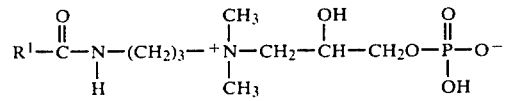

R¹ = C₇ alkyl

EXAMPLE 5

24.3 parts of Reactant "A" and 60.0 parts of water are charged in a reacting vessel under good agitation. Heat is applied to approximately 50° C. 15.4 parts of 3-caproamidopropyl dimethylamine are slowly charged to the above solution using good agitation. Heating is continued to 90°–05° C. and held at this temperature for 3 to 4 hours. Reaction reaches 97% during this time via inorganic chloride and tertiary amine analysis.

The product is an aqueous solution of a novel product having the following structure:

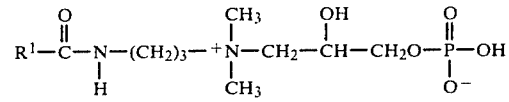

R¹ = C₅ alkyl

EXAMPLE 6

18.5 parts of Reactant "A" and 60.0 parts of water are charged in a reacting vessel under good agitation. Heat is applied to approximately 50° C. 21.5 parts of 3-oleamidopropyl dimethylamine are slowly charged to the above solution using good agitation. Heating is continued to 90°–95° C. and held at this temperature for 3 to 4 hours. Reaction reaches 97% during this time via inorganic chloride and tertiary amine analysis.

The product is an aqueous solution of a novel product having the following structure:

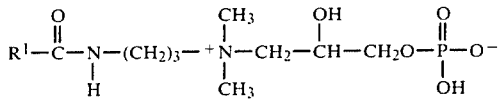

R¹ = C₁₇ alkyl

EXAMPLE 7

23.3 parts of Reactant "A" and 60.0 parts of water are charged in a reacting vessel under good agitation. Heat is applied to approximately 50° C. 16.7 parts of 3-cocamidopropyl diethylamine are slowly charged to the above solution using good agitation. Heating is continued to 90°–95° C. and held at this temperature for 3 to 4 hours. Reaction reaches 97% during this time via inorganic chloride and tertiary amine analysis.

The product is an aqueous solution of a novel product having the following structure:

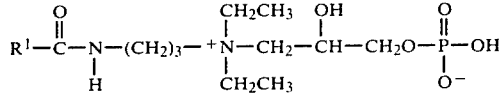

R¹ = C₇–C₁₇ alkyl

EXAMPLE 8

23.6 parts of Reactant "A" and 60.0 parts of water are charged in a reacting vessel under good agitation. Heat is applied to approximately 50° C. 16.4 parts of a blend of 70/30 3-lauramidopropyl diethylamine and 3-myristamidopropyl dimethylamine are slowly charged to the above solution using good agitation. Heating is continued to 90°–95° C. and held at this temperature for 3 to 4 hours. Reaction reaches 97% during this time via inorganic chloride and tertiary amine analysis.

The product is an aqueous solution of a novel product having the following structure:

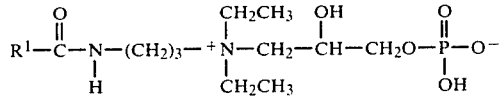

R¹ = 70% C₁₁ alkyl
30% C₁₃ alkyl

EXAMPLE 9

22.4 parts of Reactant "C" and 60.0 parts of water are charged in a reacting vessel under good agitation. Heat is applied to approximately 50° C. 17.6 parts of 3-cocamidopropyl dimethylamine are slowly charged to the above solution using good agitation. Heating is continued to 90°–95° C. and held at this temperature for 3 to 4 hours. Reaction reaches 97% during this time via inorganic chloride and tertiary amine analysis.

The product is an aqueous solution of a novel product having the following structure:

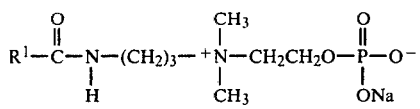

R$^1$ = C$_7$–C$_{17}$ alkyl

EXAMPLE 10

25.7 parts of Reactant "C" and 60.0 parts of water are charged in a reacting vessel under good agitation. Heat is applied to approximately 50° C. 14.3 parts of a blend of 70/30 lauramidopropyl dimethylamine and myristamidopropyl dimethylamine are slowly charged to the above solution using good agitation. Heating is continued to 90°–95° C. and held at this temperature for 3 to 4 hours. Reaction reaches 97% during this time via inorganic chloride and tertiary amine analysis.

The product is an aqueous solution of a novel product having the following structure:

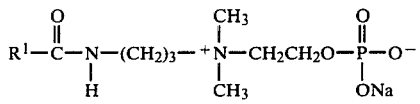

R$^1$ = 70% C$_{11}$ alkyl
30% C$_{13}$ alkyl

EXAMPLE 11

20.8 parts of Reactant "C" and 60.0 parts of water are charged in a reacting vessel under good agitation. Heat is applied to approximately 50° C. 19.2 parts of a 70/30 blend of 3-lauramidopropyl dimethylamine and 3-myristamidopropyl dimethylamine are slowly charged to the above solution using good agitation. Heating is continued to 90°–95° C. and held at this temperature for 3 to 4 hours. Reaction reaches 97% during this time via inorganic chloride and tertiary amine analysis.

The product is an aqueous solution of a novel product having the following structure:

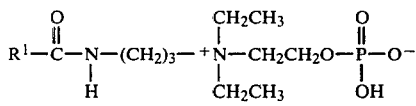

R$^1$ = 70% C$_{11}$ alkyl
10% C$_{13}$ alkyl

EXAMPLE 12

23 parts of Reactant "C" and 60.0 parts of water are charged in a reacting vessel under good agitation. Heat is applied to approximately 50° C. 17 parts of molten 3-cocamidopropyl dimethylamine are slowly charged under good agitation. Heating is continued to 90°–95° C. and held at this temperature for 3 to 4 hours. Reaction reaches 98% during this time via inorganic chloride and tertiary amine analysis.

The product is an aqueous solution of a novel product having the following structure:

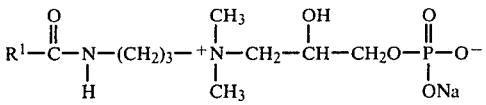

R$^1$ = C$_7$ to C$_{17}$ alkyl

EXAMPLE 13

23.4 parts of Reactant "C" and 60.0 parts of water are charged in a reacting vessel under good agitation. Heat is applied to approximately 50° C. 16.6 parts of a 70/30 blend of 3-lauramidopropyl dimethylamine and 3-myristamidopropyl dimethylamine are slowly charged to the above solution using good agitation. Heating is continued to 90°–95° C. and held at this temperature for 3 to 4 hours. Reaction reaches 98% during this time via inorganic chloride and tertiary amine analysis.

The product is an aqueous solution of a novel product having the following structure:

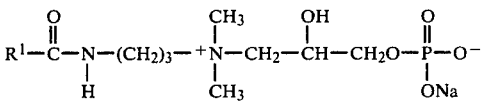

R$^1$ = 70% C$_{11}$ alkyl
30% C$_{13}$ alkyl

EXAMPLE 14

25.7 parts of Reactant "C" and 60.0 parts of water are charged in a reacting vessel under good agitation. Heat is applied to approximately 50° C. 14.3 parts of 3-lauramidopropyl dimethylamine are slowly charged to the above solution using good agitation. Heating is continued to 90°–95° C. and held at this temperature for 3 to 4 hours. Reaction reaches 98% during this time via inorganic chloride and tertiary amine analysis.

The product is an aqueous solution of a novel product having the following structure:

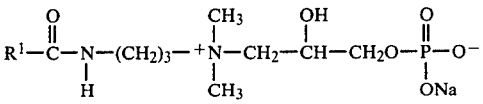

R$^1$ = C$_{11}$ alkyl

EXAMPLE 15

26.4 parts of Reactant "C" and 60.0 parts of water are charged in a reacting vessel under good agitation. Heat is applied to approximately 50° C. 13.6 parts of 3-caprylamidopropyl dimethylamine are slowly charged to the above solution using good agitation. Heating is continued to 90°–95° C. and held at this temperature for 3 to 4 hours. Reaction reaches 98% during this time via inorganic chloride and tertiary amine analysis.

The product is an aqueous solution of a novel product having the following structure:

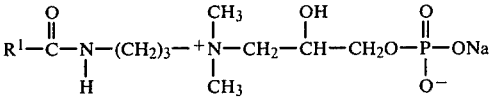

R = C$_7$ alkyl

EXAMPLE 16

26.8 part of Reactant "C" and 60.0 parts of water are charged in a reacting vessel under good agitation. Heat is applied to approximately 50° C. 13.2 parts of 3-caproamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

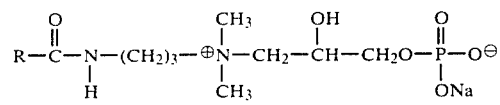

R = $C_5$ alkyl

EXAMPLE 17

21.0 parts of Reactant "B" and 60.0 parts of water are charged in a reacting vessel under good agitation. Heat is applied to approximately 50° C. 19.0 parts of 3-oleamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

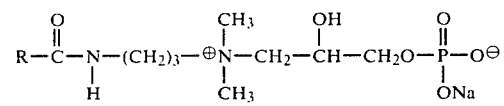

R = $C_{17}$ alkyl

EXAMPLE 18

25.8 parts of Reactant "C" and 60.0 parts of water are charged in a reacting vessel under good agitation. Heat is applied to approximately 50° C. 14.2 parts of 3-cocamidopropyl diethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

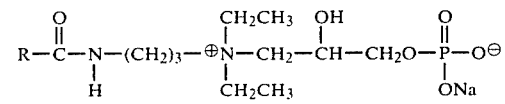

R = $C_7$–$C_{17}$ alkyl

EXAMPLE 19

26.2 parts of Reactant "C" and 60.0 parts of water are charged in a reacting vessel under good agitation. Heat is applied to approximately 50° C. 13.8 parts of a 70/30 blend of 3-lauramidopropyl diethylamine and 3-myristamidopropyl diethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

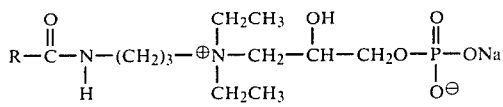

R = 70% $C_{11}$ alkyl
30% $C_{13}$ alkyl

EXAMPLE 20

20.4 parts of Reactant "B" and 60.0 parts of water are charged in a reacting vessel under good agitation. Heat is applied to 50° C. 19.6 parts of molten 3-cocamidopropyl dimethylamine are slowly charged under good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

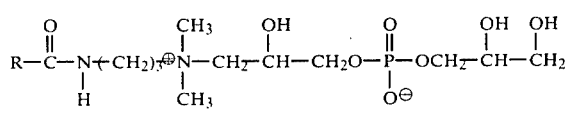

R = $C_7$–$C_{17}$ alkyl

EXAMPLE 21

20.8 parts of Reactant "B" and 60.0 parts of water are charged in a reacting vessel under good agitation. Heat is applied to approximately 50° C. 19.2 parts of a 70/30 blend of 3-lauramidopropyl dimethylamine and 3-myristamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

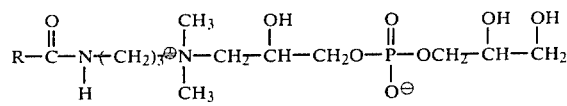

R = 70% $C_{11}$ alkyl
30% $C_{13}$ alkyl

EXAMPLE 22

23.1 parts of Reactant "B" and 60.0 parts of water are charged in a reacting vessel under good agitation. Heat is applied to approximately 50° C. 16.9 parts of 3-lauramidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis The product is an aqueous solution of a novel product having the following structure.

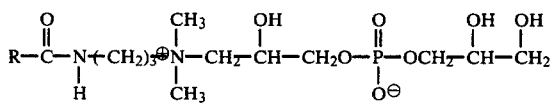

R = C$_{11}$ alkyl

EXAMPLE 23

23.2 parts of Reactant "B" and 60.0 parts of water are charged in a reacting vessel under good agitation. Heat is applied to approximately 50° C. 16.2 parts of 3-caprylamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

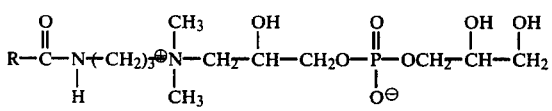

R = C$_7$ alkyl

EXAMPLE 24

24.3 parts of Reactant "B" and 60.0 parts of water are charged in a reacting vessel under good agitation. Heat is applied to approximately 50° C. 15.7 parts of 3-caproamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

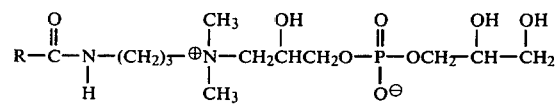

R = C$_5$

EXAMPLE 25

21.6 parts of Reactant "B" and 60.0 parts of water are charged in a reacting vessel under good agitation. Heat is applied to approximately 50° C. 18.4 parts of 3-oleamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

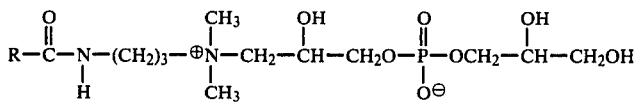

R = C$_{17}$ alkyl

EXAMPLE 26

26.8 parts of Reactant "B" and 60.0 parts of water are charged in a reacting vessel under good agitation. Heat is applied to approximately 50° C. 13.2 parts of 3-cocamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

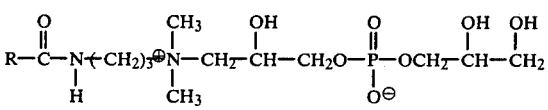

R = C$_7$–C$_{17}$ alkyl

EXAMPLE 27

26.4 parts of Reactant "B" and 60.0 parts of water are charged in a reacting vessel under good agitation. Heat is applied to approximately 50° C. 13.6 parts of a 70/30 blend of 3-lauramidopropyl diethylamine and 3-myristamidopropyl diethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

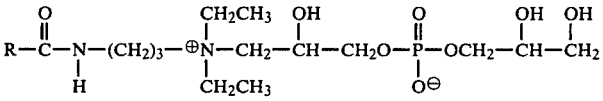

R = 70% C$_{11}$ alkyl
30% C$_{13}$ alkyl

EXAMPLE 28

14.4 parts of Reactant "D" and 60.0 parts of water are charged in a reacting vessel under good agitation. Heat is applied to 50° C. 25.6 parts of molten 3-cocamidopropyl dimethylamine are slowly charged under good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

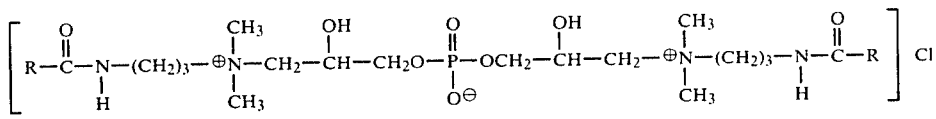

R = $C_7$–$C_{17}$ alkyl

EXAMPLE 29

15.3 parts of Reactant "D" and 60.0 parts of water are charged in a reacting vessel under good agitation. Heat is applied to approximately 50° C. 24.7 parts of 70/30 blend of 3-lauramidopropyl dimethylamine and 3-myristamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

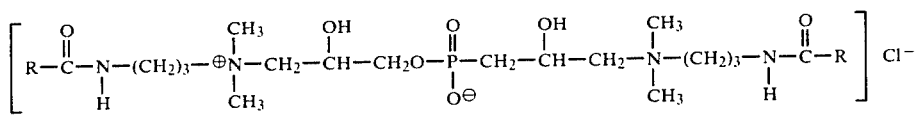

R = 70% $C_{11}$ alkyl
30% $C_{13}$ alkyl

EXAMPLE 30

20.7 parts of Reactant "D" and 60.0 parts of water are charged in a reacting vessel under good agitation. Heat is applied to approximately 50° C. 19.3 parts of 3-caprylamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

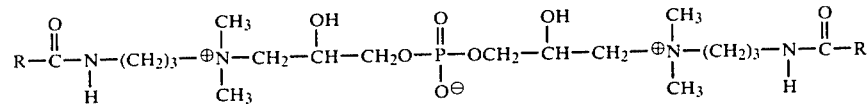

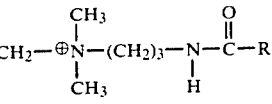

R = $C_7$ alkyl

EXAMPLE 31

30.3 parts of Reactant "D" and 60.0 parts of water are charged in a reacting vessel under good agitation. Heat is applied to approximately 50° C. 9.7 parts of 3-caproamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

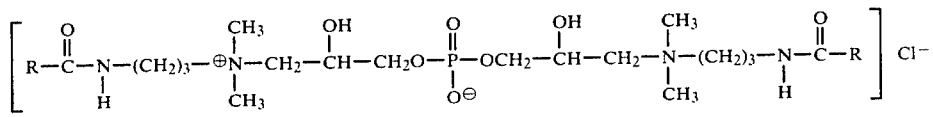

R = $C_5$ alkyl

EXAMPLE 32

16.0 parts of Reactant "D" and 60.0 parts of water are charged in a reacting vessel under good agitation. Heat is applied to approximately 50° C. 24.0 parts of 3-oleamidopropyl dimethylamine are slowly charged to the above solution using good agitation. Heating is continued to 90°–95° C. and the heated mixture held at this temperature for 3 to 4 hours. Reaction reaches 98% during this time via inorganic chloride and tertiary amine analysis.

The product is an aqueous solution of a novel product having the following structure:

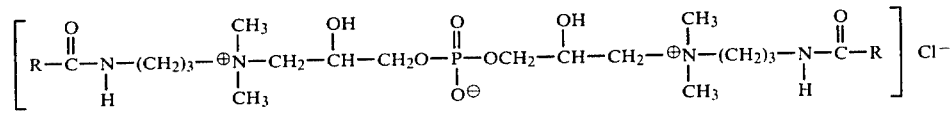

R = $C_{17}$ alkyl

EXAMPLE 33

20.70 parts of Reactant "B" and 60.0 parts of soft water are charged into a suitable reactor under good agitation. Heat is applied to 50° C. 19.30 parts of 2-undecyl-1-hydroxyethyl propionic acid imidazoline are charged under good agitation and heating is continued to 90°-95° C. and the heated mixture held at this temperature for 4 hours. The reaction is complete when inorganic chloride reaches 97% of theoretical.

The product is an aqueous solution of a novel product having the following structure:

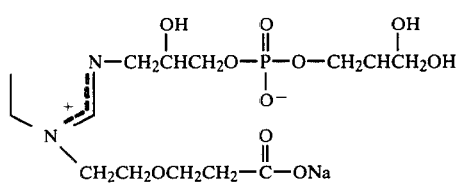

R=C₁₁

EXAMPLE 34

27.9 parts of Reactant "D" and 60.0 parts of water are charged in a reacting vessel under good agitation. Heat is applied to approximately 50° C. 12.1 parts of 3-caproamidopropyl diethylamine are slowly charged to the above solution using good agitation. Heating is continued to 90°-95° C. and the heated mixture held at this temperature for 3 to 4 hours. Reaction reaches 98% during this time via inorganic chloride and tertiary amine analysis.

The product is an aqueous solution of a novel product having the following structure:

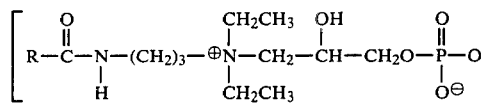

R=C₇ alkyl

EXAMPLE 35

21.7 parts of Reactant "C" and 60.0 parts of water are charging into a reacting vessel under good agitation. Heat is applied to approximately 50° C. 18.3 parts of a 70/30 blend of lauramido ethyl 2,6-dimethyl morphline and myristamido ethyl 2,6-dimethyl morphline are slowly charged to the above solution using good agitation. Heating is continued to 90°-95° C. and the heated mixture held at this temperature for 3 to 4 hours. Reaction reaches 98% during this time via inorganic chloride and tertiary amine analysis.

The product is an aqueous solution of a novel product having the following structure

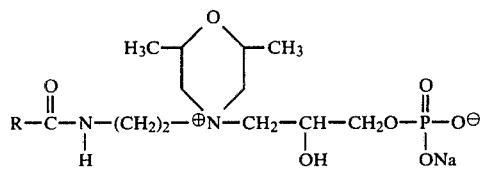

R=70% C₁₁ alkyl 30% C₁₃ alkyl

EXAMPLE 36

26.7 parts of Reactant "C" and 60.0 parts of water are charged into a reacting vessel under good agitation. Heat is applied to approximately 50° C. 13.3 parts of 3-benzamido propyl dimethylamine are slowly charged to the above solution using good agitation. Heating is continued to 90°-95° C. and the heated mixture held at this temperature for 3 to 4 hours. Reaction reaches 98% during this time via inorganic chloride and tertiary amine analysis:

The product is an aqueous solution of a novel product having the following structure:

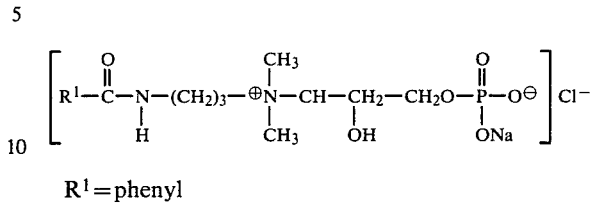

R¹=phenyl

EXAMPLE 37

22.88 parts of Reactant "A" and 60.0 parts water are charged into a suitable reaction vessel under good agitation. Heat is applied to 50° C. 17.12 parts of 1-hydroxyethyl-2-alkyl-2-imidazoline (the alkyl has 7+17 carbon atoms) are charged under good agitation. Heating is continued to 90°-95° C. and the heated mixture held at this temperature for 4 hours. Reaction reaches 97% during this time via inorganic chloride and tertiary amine analysis.

The product is an aqueous solution of a novel product having the following structure:

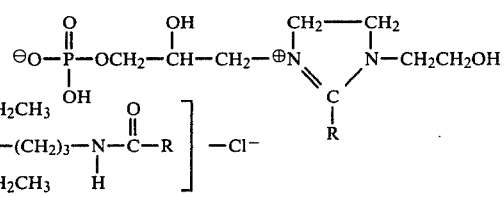

R=C₇ to C₁₇ alkyl

EXAMPLE 38

20.8 parts of Reactant "A" and 60.0 parts of water are charged into a suitable reaction vessel under good agitation. Heat is applied to 50° C. 19.2 parts of 1-hydroxyethyl 2-alkyl-2-imidazoline (being C₁₇) are charged under good agitation. Heating is continued to 90°-95° C. and the heated mixture held at this temperature for 4 hours. Reaction reaches 97% during this time via inorganic chloride and tertiary amine analysis.

The product is an aqueous solution of a novel product having the following structure:

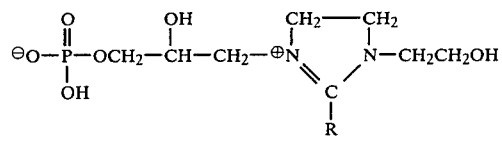

R=C₁₇ alkyl

EXAMPLE 39

21.45 parts of Reactant "A" and 60.0 parts water are charged into a suitable reaction vessel under good agitation. Heat is applied to 50° C. 18.55 parts of 1-hydroxyethyl-2-alkyl-2-imidazoline (being 70% C₁₁ and 30%

$C_{13}$) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

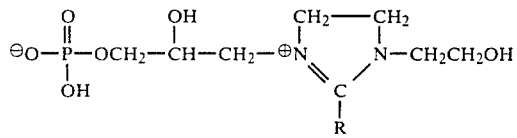

R = $C_{11}$ — 70% alkyl
$C_{13}$ — 30% alkyl

EXAMPLE 40

23.32 parts of Reactant "A" and 60.0 parts water are charged into a suitable reaction vessel under good agitation. Heat is applied to 50° C. 16.68 parts of 1-hydroxyethyl-2-alkyl-2-imidazoline (being $C_{11}$) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

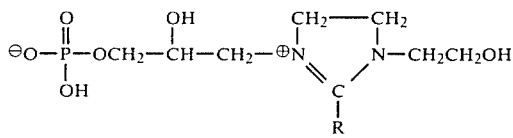

R = $C_{11}$

EXAMPLE 41

26.0 parts of Reactant "A" and 60.0 parts water are charged into a suitable reaction vessel under good agitation. Heat is applied to 50° C. 14.0 parts of 1-hydroxyethyl-2-alkyl-2-imidazoline (being $C_{11}$) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

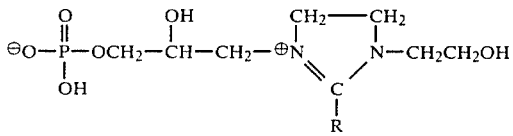

R = $C_7$

EXAMPLE 42

27.56 parts of Reactant "A" and 60.0 parts water are charged into a suitable reaction vessel under good agitation. Heat is applied to 50° C. 12.44 parts of 1-hydroxyethyl-2-alkyl-2-imidazoline (being $C_5$) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

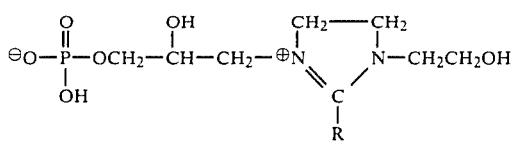

R = $C_5$ alkyl

EXAMPLE 43

19.72 parts of Reactant "I" and 60.0 parts of water are charged into a suitable reaction vessel under good agitation. Heat is applied to 50° C. 20.28 parts of 3-cocamidopropyl dimethylamine are charged under good agitation. Heating is continued to 90°–95° C. and the heated mixture held at this temperature for 4 hours. Reaction is complete when inorganic chloride reaches theoretical and residual 3° N is vanishingly small.

The produce is an aqueous solution of a novel product having the following structure:

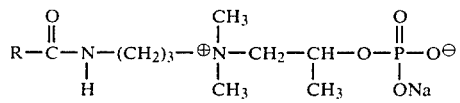

and

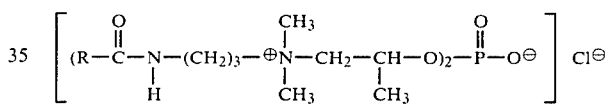

R = $C_7$ to $C_{17}$ alkyl

EXAMPLE 44

20.69 parts of Reactant "I" and 60.0 parts of water are charged into a suitable reaction vessel under good agitation. Heat is applied to 50° C. 19.31 parts of 1-hydroxyethyl-2-alkyl-2-imidazoline* are charged under good agitation. Heating is continued to 90°–95° C. and the heated mixture held at this temperature for 4 hours. Reaction is complete when inorganic chloride reaches theoretical and residual 3° N is vanishingly small.

*(alkyl being $C_7$ to $C_{17}$)

The product is an aqueous solution of a novel product having the following structure:

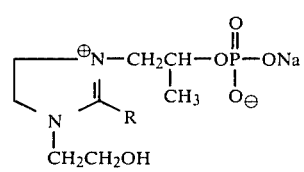

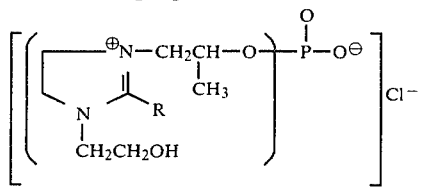

R = $C_7$ to $C_{17}$ alkyl

EXAMPLE 45

20.72 parts of Reactant "F" and 60.0 parts of water are charged into a suitable reaction vessel under good agitation. Heat is applied to 50° C. 19.28 parts of 3-cocamidopropyl dimethylamine are charged under good agitation. Heating is continued to 90°–95° C. and the heated mixture held at this temperature for 4 hours. Reaction is complete when inorganic chloride reaches theoretical and residual 3° N is vanishingly small.

The product is an aqueous solution of a novel product having the following structure:

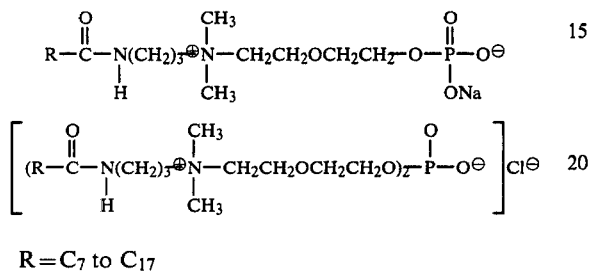

$R = C_7$ to $C_{17}$

EXAMPLE 46

21.70 parts of Reactant "F" and 60.0 parts of water are charged into a suitable reaction vessel under good agitation. Heat is applied to 50° C. 18.30 parts of 1-hydroxyethyl 2-alkyl-2-imidazoline* are charged under good agitation. Heating is continued to 90°–95° C. and the heated mixture is held at this temperature for 4 hours. Reaction is complete when inorganic chloride reaches theoretical and residual 3° N is vanishingly small.
*(alkyl being $C_7$ to $C_{17}$)

The product is an aqueous solution of a novel product having the following structure:

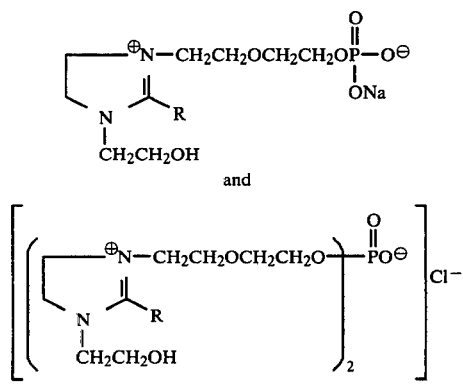

$R = C_7$ to $C_{17}$

EXAMPLE 47

20.30 parts of Reactant "G" and 60.0 parts of water are charged into a suitable reaction vessel under good agitation. Heat is applied to 50° C. 19.70 parts of 3-cocamidopropyl dimethyamine are charged under good agitation. Heating is continued to 90°–95° C. and the heated mixture held at this temperature for 4 hours. Reaction is complete when inorganic chloride reaches theoretical and residual 3° N is vanishingly small.

The product is an aqueous solution of a novel product having the following structure:

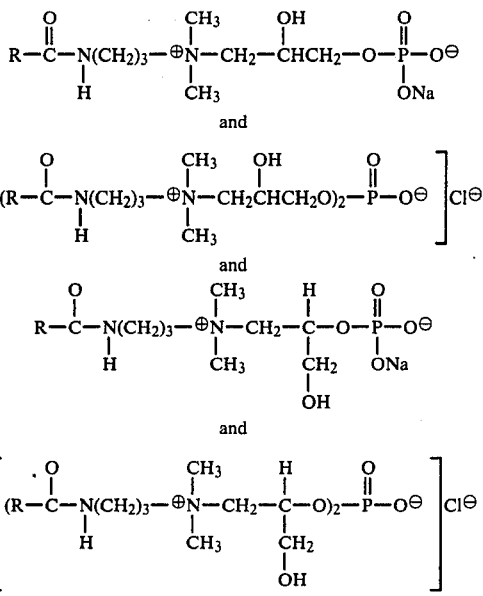

$R = C_7$ to $C_{17}$ alkyl

EXAMPLE 48

20.90 parts of Reactant "H" and 60.0 parts of water are charged into a suitable reaction vessel under good agitation. Heat is applied to 50° C. 19.10 parts of 3-cocamidopropyl dimethamine are charged under good agitation. Heating is continued to 90°–95° C. and the heated mixture held at this temperature for 4 hours. Reaction is complete when inorganic chloride reaches theoretica and residual 3° N is vanishingly small.

The product is an aqueous solution of a novel product having the following structure:

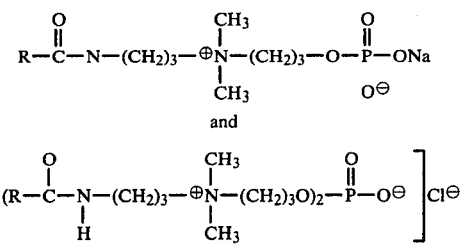

$R = C_7$ to $C_{17}$ alkyl

EXAMPLE 49

23.9 parts of Reactant "C" and 60.0 parts water are charged into a suitable reaction vessel under good agitation. Heat is applied to 50° C. 16.1 parts of 1-hydroxyethyl-2-alkyl-2-imidazoline (alkyl having 7-17 carbons) are charged under good agitation. Heating is continued to 90°–95° C. and the heated mixture is held at this temperature for 4 hours. Reaction reaches 97% during this time via inorganic chloride and tertiary amine analysis.

The product is an aqueous solution of a novel product having the following structure:

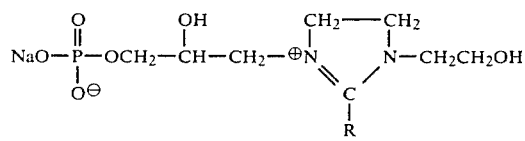

R = C₇ to C₁₇ alkyl

EXAMPLE 50

20.2 parts of Reactant "C" and 60.0 parts water are charged into a suitable reaction vessel under good agitation. Heat is applied to 50° C. 19.8 parts of 1 hydroxyethyl-2-alkyl-2-imidazoline (being C₁₇) are charged under good agitation. Heating is continued to 90°–95° C. and the heated mixture held at this temperature for 4 hours. Reaction reaches 97% during this time via inorganic chloride and tertiary amine analysis The product is an aqueous solution of a novel product having the following structure:

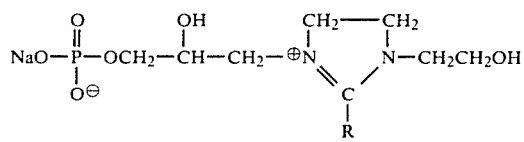

R = C₁₇ alkyl

EXAMPLE 51

22.4 parts of Reactant "C" and 60.0 parts water are charged into a suitable reaction vessel under good agitation. Heat is applied to 50° C. 17.6 parts of 1-hydroxyethyl-2-alkyl-2-imidazoline (being C₁₁) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

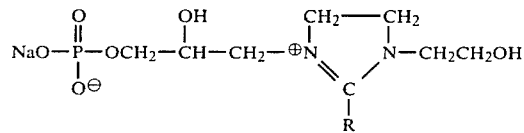

R = C₁₁ 70% alkyl
C₁₃ 30% alkyl

EXAMPLE 52

24.3 parts of Reactant "C" and 60.0 parts water are charged into a suitable reaction vessel under good agitation. Heat is applied to 50° C. 17.5 parts of 1-hydroxyethyl-2-alkyl-2-imidazoline (being C₁₁) are charged under good agitation. Heating is continued to 90°–95° C. and the heated mixture held at this temperature for 4 hours. Reaction reaches 97% during this time via inorganic chloride and tertiary amine analysis.

The produce is an aqueous solution of a novel product having the following structure:

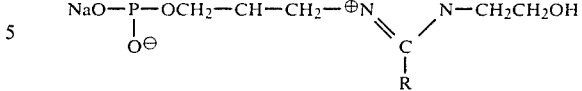

R = C₁₁ alkyl

EXAMPLE 53

26.9 parts of Reactant "C" and 60.0 parts water are charged into a suitable reaction vessel under good agitation. Heat is applied to 50° C. 13.1 parts of 1-hydroxyethyl-2-alkyl-2-imidazoline (being C₇) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

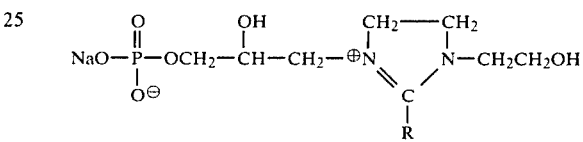

R = C₇ alkyl

EXAMPLE 54

28.4 parts of Reactant "C" and 60.0 parts water are charged into a suitable reaction vessel under good agitation. Heat is applied to 50° C. 11.6 parts of 1-hydroxyethyl-2-alkyl-2-imidazoline (being C₅) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

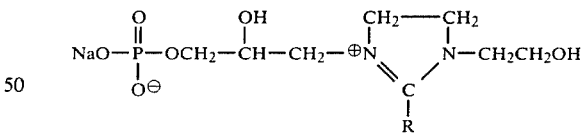

R = C₅ alkyl

EXAMPLE 55

25.0 parts of Reactant "B" and 60.0 parts water are charged into a suitable reaction vessel under good agitation. Heat is applied to 50° C. 15.0 parts of 1-hydroxyethyl-2-alkyl-2-imidazoline (alkyl having 7–17 carbons) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

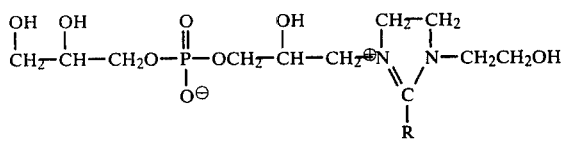

R = C₇ to C₁₇ alkyl

EXAMPLE 56

21.4 parts of Reactant "B" and 60.0 parts water are charged into a suitable reaction vessel under good agitation. Heat is applied to 50° C. 18.6 parts of 1-hydroxyethyl-2-alkyl-2-imidazoline (being C₁₇) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

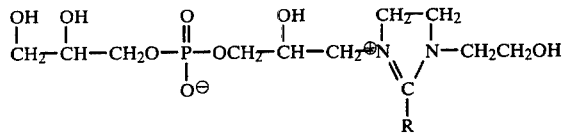

R = C₁₇ alkyl

EXAMPLE 57

23.6 parts of Reactant "B" and 60.0 parts water are charged into a suitable reaction vessel under good agitation. Heat is applied to 50° C. 16.4 parts of 1-hydroxyethyl-2-alkyl-2-imidazoline (being 70% C₁₁ and 30% C₁₃) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

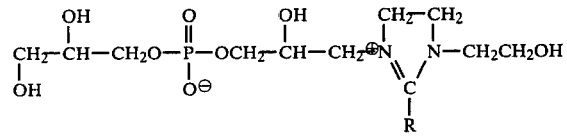

R = C₁₁-70% alkyl
C₁₃-30% alkyl

EXAMPLE 58

25.4 parts of Reactant "B" and 60.0 parts water are charged into a suitable reaction vessel under good agitation. Heat is applied to 50° C. 14.6 parts of 1-hydroxyethyl-2-alkyl-2-imidazoline (being C₁₁) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

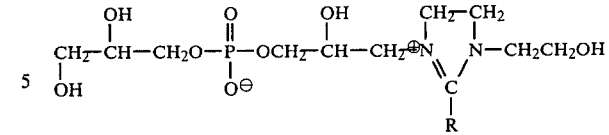

R = C₁₁ alkyl

EXAMPLE 59

27.9 parts of Reactant "B" and 60.0 parts water are charged into a suitable reaction vessel under good agitation. Heat is applied to 50° C. 12.1 parts of 1-hydroxyethyl-2-alkyl-2-imidazoline (being C₇) are charged under good agitation. Heating is continued for 4 hours. Reaction reaches 97% during this time via inorganic chloride and tertiary amine analysis.

The product is an aqueous solution of a novel product having the following structure:

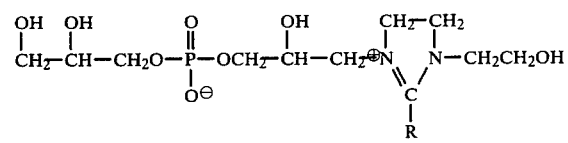

R = C₇ alkyl

EXAMPLE 60

29.4 parts of Reactant "B" and 60.0 parts water are charged into a suitable reaction vessel under good agitation. Heat is applied to 50° C. 10.6 parts of 1-hydroxyethyl-2-alkyl-2-imidazoline (being C₅) are charged under good agitation. Heating is continued for 4 hours. Reaction reaches 97% during this time via inorganic chloride and tertiary amine analysis.

The product is an aqueous solution of a novel product having the following structure:

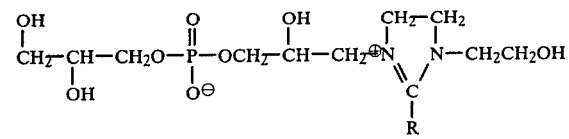

R = C₅ alkyl

EXAMPLE 61

25.8 parts of Reactant "B" and 60.0 parts water are charged into a suitable reaction vessel under good agitation. Heat is applied to 50° C. 14.2 parts of alkyldimethylamine (alkyl being C₁₂) are charged under good agitation. Heating is continued to 90°–95° C. and the heated mixture held at this temperature for 4 hours. Reaction reaches 97% during this time via inorganic chloride and tertiary amine analysis.

The produce is an aqueous solution of a novel product having the following structure:

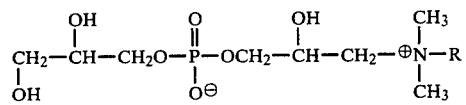

R = C₁₂

EXAMPLE 62

18.04 parts of Reactant "C" and 60.0 parts of water are charged into a suitable reaction vessel under good agitation. Heat is applied to 50° C. 21.96 parts of N-alkylamidoethyl-N-hydroxyethyl-glycine (alkyl being 70% $C_{11}$ and 30% $C_{13}$) are charged under good agitation. Heating is continued to 90°–95° C. and the heated mixture held at this temperature for 4 hours. Reaction is complete when inorganic chloride reaches theoretical and residual 3° N is vanishingly small.

The product is an aqueous solution of a novel product having the following structure:

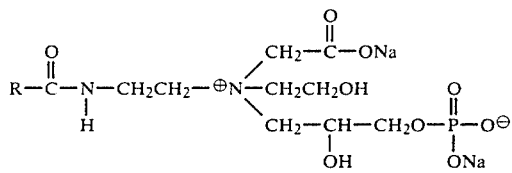

R = 70/30 Lauric/Myristic

EXAMPLE 63

25.6 parts of Reactant "D" and 60.0 parts water are charged into a suitable reaction vessel under good agitation. Heat is applied to 50° C. 14.4 parts of 1-hydroxyethyl-2-alkyl-2-imidazoline (alkyl having 7–17 carbons) are charged under good agitation. Heating is continued to 90°–95° C. and the heated mixture held at this temperature for 4 hours. Reaction reaches 97% during this time via inorganic chloride and tertiary amine analysis.

The product is an aqueous solution of one of the novel products having the following structure:

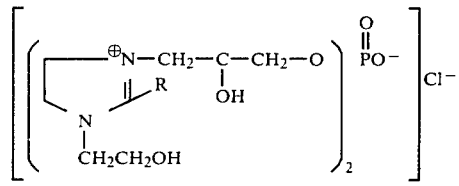

R = $C_7$ to $C_{17}$ alkyl

EXAMPLE 64

22.0 parts of Reactant "D" and 60.0 parts water are charged into a suitable reaction vessel under good agitation. Heat is applied to 50° C. 18.0 parts of 1-hydroxyethyl-2-alkyl-2-imidazoline (being $C_{17}$) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

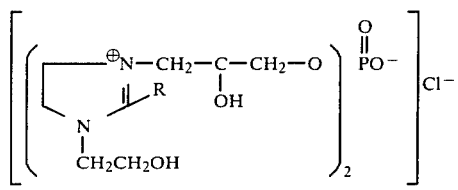

R = $C_{17}$ alkyl

EXAMPLE 65

24.2 parts of Reactant "D" and 60.0 parts water are charged into a suitable reaction vessel under good agitation. Heat is applied to 50° C. 15.8 parts of 1-hydroxyethyl-2-alkyl-2-imidazoline (being 70% $C_{11}$, 30% $C_{13}$) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

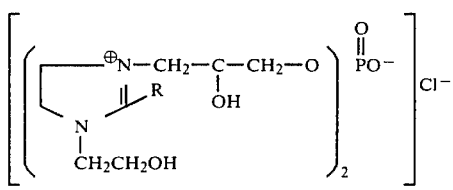

R = $C_{11}$-70% alkyl
$C_{13}$-30% alkyl

EXAMPLE 66

26.0 parts of Reactant "D" and 60.0 parts of water are charged into a suitable reaction vessel under good agitation. Heat is applied to 50° C. 14.0 parts of 1-hydroxyethyl-2-alkyl-2-imidazoline (being $C_{11}$) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

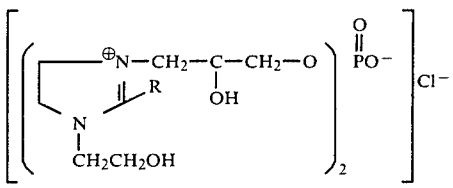

R = $C_{11}$ alkyl

EXAMPLE 67

28.5 parts of Reactant "D" and 60.0 parts of water are charged into a suitable reaction vessel under good agitation. Heat is applied to 50° C. 11.5 parts of 1-hydroxyethyl-2-alkyl-2-imidazoline (being $C_7$) are charged under good agitation. Heating is continued to 90°–95° C. and the heated mixture held at this temperature for 4 hours. Reaction reaches 97% during this time via inorganic chloride and tertiary amine analysis.

The product is an aqueous solution of a novel product having the following structure:

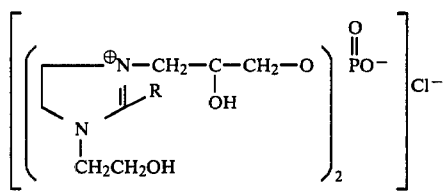

R = C₇ alkyl

EXAMPLE 68

22.61 parts of Reactant "G" and 60.0 parts of water are charged into a suitable reaction vessel under good agitation. Heat is applied to 50° C. 17.39 parts of 1-hydroxyethyl-2-alkyl-2-imidazoline (alkyl being C₇ to C₁₇) are charged under good agitation. Heating is continued to 90°–95° C. and the heated mixture held at this temperature for 4 hours. Reaction is complete when inorganic chloride reaches theoretical and residual 3° N is vanishingly small.

The product is an aqueous solution of a novel product having the following structure:

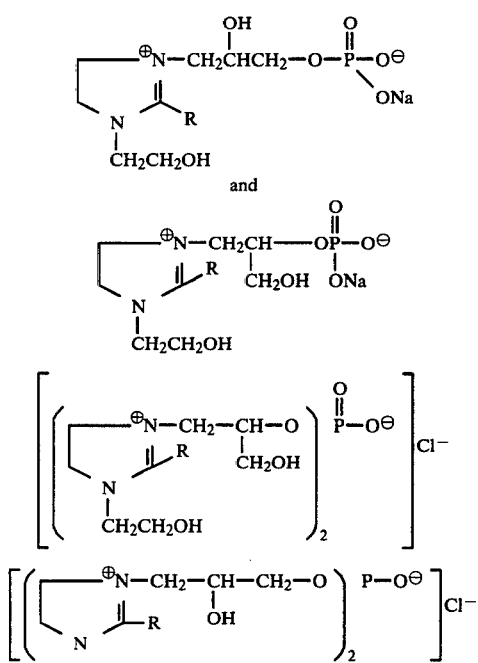

R = C₇ to C₁₇ alkyl

EXAMPLE 69

21.87 parts of Reactant "H" and 60.0 parts of water are charged into a suitable reaction vessel under good agitation. Heat is applied to 50° C. 18.13 parts of 1-hydroxyethyl-2-alkyl-2-imidazoline (alkyl being C₇ to C₁₇) are charged under good agitation. Heating is continued to 90°–95° C. and the heated mixture held at this temperature for 4 hours. Reaction is complete when inorganic chloride reaches theoretical and residual 3° N is vanishingly small.

The product is an aqueous solution of a novel product having the following structure:

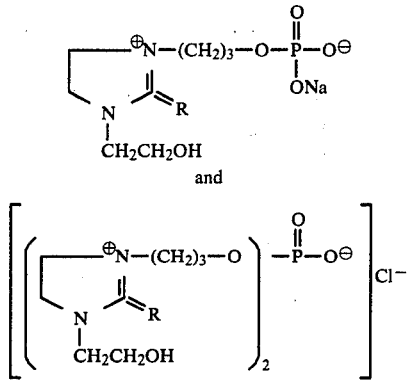

R = C₇ to C₁₇

EXAMPLE 70

20.53 parts of Reactant "F" and 60.0 parts of water are charged into a suitable reaction vessel under good agitation. Heat is applied to 50° C. 19.47 parts of 3-lauramidopropyl diethylamine are charged under good agitation. Heating is continued to 90°–95° C. and the heated mixture held at this temperature for 4 hours. Reaction is complete when inorganic chloride reaches theoretical and residual 3° N is vanishingly small.

The product is an aqueous solution of a novel product having the following structure:

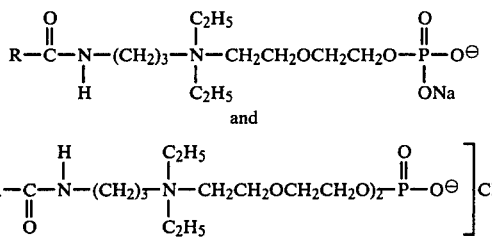

R = C₁₁ alkyl

EXAMPLE 71

21.47 parts of Reactant "F" and 60.0 parts of water are charged into a suitable reaction vessel under good agitation. Heat is applied to 50° C. 18.53 parts of 3-lauramidopropyl dimethylamine are charged under good agitation. Heating is continued to 90°–95° C. and the heated mixture held at this temperature for 4 hours. Reaction is complete when inorganic chloride reaches theoretical and residual 3° N is vanishingly small.

The product is an aqueous solution of a novel product having the following structure:

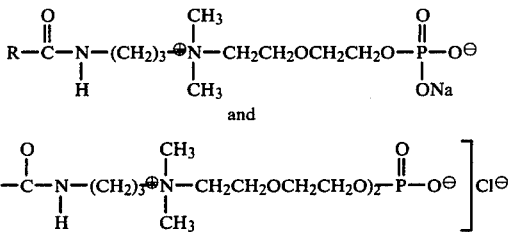

R = C₁₁ alkyl

EXAMPLE 72

21.00 parts of Reactant "G" and 60.0 parts of water are charged into a suitable reaction vessel under good agitation. Heat is applied to 50° C. 19.0 parts of 3-lauramidopropyl dimethylamine are charged under good agitation. Heating is continued to 90°–95° C. and the heated mixture held at this temperature for 4 hours. Reaction is complete when inorganic chloride reaches theoretical and residual 3° N is vanishingly small.

The product is an aqueous solution of a novel product having the following structure:

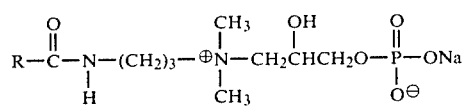

and

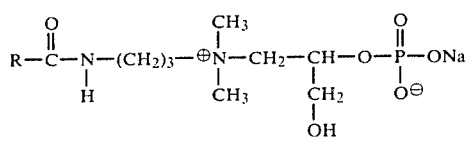

and

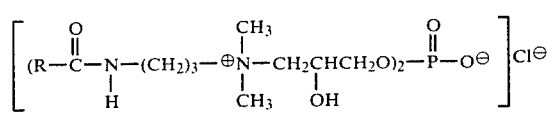

and

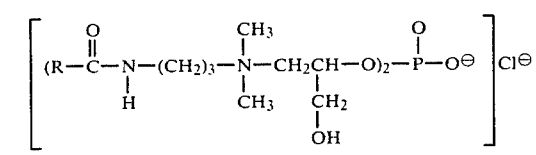

$R = C_{11}$ alkyl

EXAMPLE 73

18.29 parts of Reactant "C" and 60.0 parts of water are charged into a suitable reaction vessel under good agitation. Heat is applied to 50° C. 21.71 parts of N-alkamidoethyl-N-hydroxyethyl-glycine (alkyl being lauric) are charged under good agitation. Heating is continued to 90°–95° C. and the heated mixture held at this temperature for 4 hours. Reaction is complete when inorganic chloride reaches theoretical and residual 3° N is vanishingly small.

The product is an aqueous solution of a novel product having the following structure:

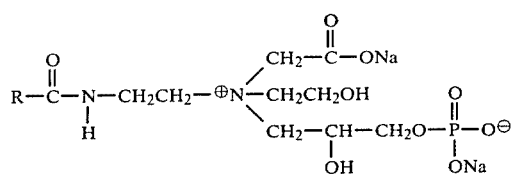

$R = C_{11}$ alkyl

EXAMPLE 74

17.48 parts of Reactant "C" and 60.0 parts of water are charged into a suitable reaction vessel under good agitation. Heat is applied to 50° C. 22.52 parts of N-alkylamidoethyl-N-hydroxyethyl-glycine (alkyl being $C_7$ to $C_{17}$) are charged under good agitation. Heating is continued to 90°–95° C. and the heated mixture held at this temperature for 4 hours. Reaction is complete when inorganic chloride reaches theoretical and residual 3° N is vanishing small.

The product is an aqueous solution of a novel product having the following structure:

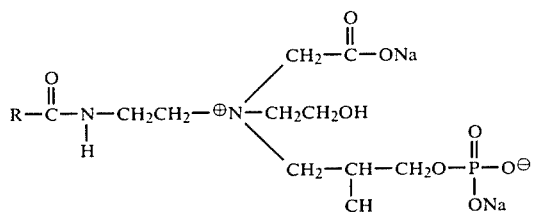

$R = C_7$ to $C_{17}$

EXAMPLE 75

18.73 parts of Reactant "B" and 60.0 parts of water are charged into a suitable reaction vessel under good agitation. Heat is applied to 50° C. 21.27 parts of N-alkylethyl-N-hydroxyethyl-glycine (alkyl being lauric) are charged under good agitation. Heating is continued to 90°–95° C. and the heated mixture held at this temperature for 4 hours. Reaction is complete when inorganic chloride reaches theoretical and residual 3° N is vanishingly small.

The product is an aqueous solution of a novel product having the following structure:

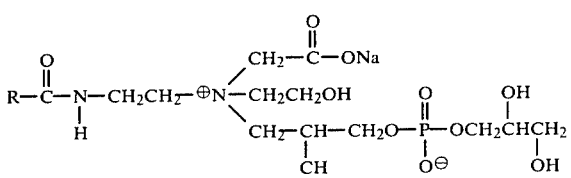

$R = C_{11}$ alkyl

EXAMPLE 76

12.69 parts of Reactant "D" and 60.0 parts of water are charged into a suitable reaction vessel under good agitation. Heat is applied to 50° C. 27.31 parts of N-alkylamidoethyl-N-hydroxyethyl-glycine (alkyl being lauric) are charged under good agitation. Heating is continued to 90°–95° C. and the heated mixture held at this temperature for 4 hours. Reaction is complete when inorganic chloride reaches theoretical and residual 3° N is vanishingly small.

The product is an aqueous solution of a novel product having the following structure:

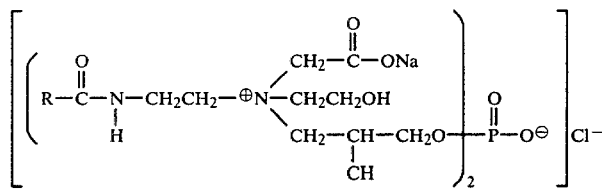

R = C₁₁ alkyl

EXAMPLE 77

15.73 parts of Reactant "A" and 60.0 parts of water are charged into a suitable reaction vessel under good agitation. Heat is applied to 50° C. 24.27 parts of N-alkylamidoethyl-N-hydroxyethyl-glycine (alkyl being myristic) are charged under good agitation. Heating is continued to 90°–95° C. and the heated mixture held at this temperature for 4 hours. Reaction is complete when inorganic chloride reaches theoretical and residual 3° N is vanishingly small.

The product is an aqueous solution of novel product having the following structure:

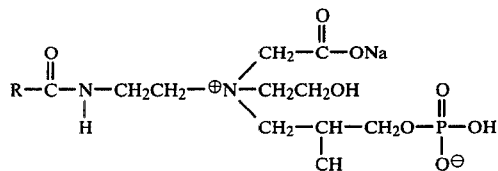

R = C₁₁ alkyl

EXAMPLE 78

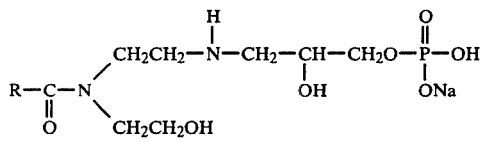

To 22.49 parts of 2-aminoethyl, 2-hydroxyethyl cocamide were charged 60.00 parts of soft water in a reactor under good agitation. The reaction mixture was heated to 50° C. and charged with 14.74 parts of Reactant "A" and 2.77 parts of sodium hydroxide. This mixture was heated to 90°–95° C. and held within this temperature range until completion. The reaction was considered complete when theoretical inorganic chloride was generated.

R = C₇ to C₁₇

EXAMPLE 79

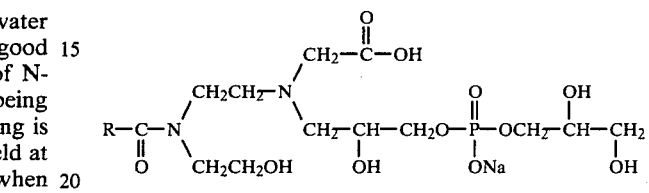

To 26.33 parts of N-(N-hydroxyethyl cocamidoethyl)glycine, were charged 60.00 parts of soft water in a reactor under good agitation. The reaction mixture was heated to 50° C. and charged with 12.00 parts of Reactant "B" and 1.67 parts of sodium hydroxide. This mixture was heated to 90°–95° C. and held within this temperature range until completion. The reaction was considered complete when theoretical inorganic chloride was generated.

R = C₇ to C₁₇

EXAMPLE 80

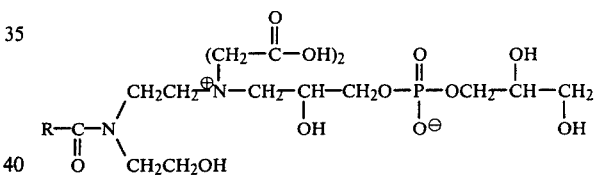

To 24.20 parts of N-(N-hydroxyethyl cocamidoethyl)N-carboxymethyl glycine, were charged 60.00 parts of soft water in a reactor under good agitation. The reaction mixture was heated to 50° C. and charged with 15.80 parts of Reactant "B". This mixture was heated to 90°–95° and held within this temperature range until completion. The reaction was considered complete when theoretical inorganic chloride was generated.

R = C₇ to C₁₇

EXAMPLE 81

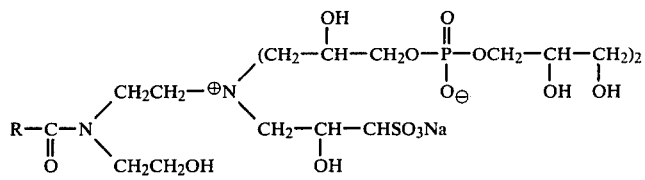

To 23.86 parts of 2-(N-hydroxyethyl-cocamido)ethylamino-2-hydroxy-3-sulfonate, were charged 60.00 parts of soft water in a reactor under good agitation. The reaction mixture was heated to 50° C. and charged with 14.17 parts of Reactant "B" and 1.97 parts of sodium hydroxide. This mixture was heated to 90°–95° C.

and held within this temperature range until completion. The reaction was considered complete when theoretical inorganic chloride was generated.
R=C₇ to C₁₇

EXAMPLE 82

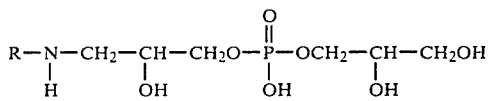

To 14.17 parts of cocamine, were charged 60.00 parts of soft water in a reactor under good agitation. The reaction mixture was heated to 50° C. and charged with 22.68 parts of Reactant "B" and 3.15 parts of sodium hydroxide. This mixture was heated to 90°–95° C. and held within this temperature range until completion. The reaction was considered complete when theoretical inorganic chloride was generated.
R=C₇ to C₁₇

EXAMPLE 83

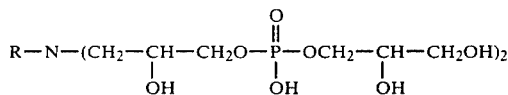

To 8.61 parts of cocamine, were charged 60.00 parts of soft water in a reactor under good agitation. The reaction mixture was heated to 50° C. and charged with 27.56 parts of Reactant "B" and 3.83 parts of sodium hydroxide. This mixture was heated to 90°–95° C. and held within this temperature range until completion. The reaction was considered complete when theoretical inorganic chloride was generated.
R=C₇ to C₁₇

EXAMPLE 84

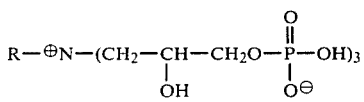

To 6.40 parts primary cocoamine, were charged 60.00 parts of soft water in a reactor under good agitation. The reaction mixture was heated to 50° C. and charged with 30.74 parts of Reactant "A" and 2.86 parts of sodium hydroxide. This mixture was heated to 90°–95° C. and held within this temperature range until completion. The reaction was considered complete when theoretical inorganic chloride was generated.
R=C₇ to C₁₇

EXAMPLE 85

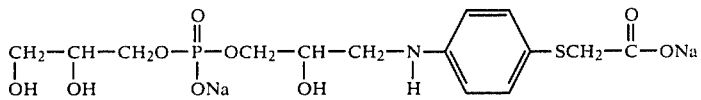

To 14.32 parts of p-amino-phenylmercaptoacetic acid, were charged 60.00 parts of soft water in a reactor under good agitation. The reaction mixture was heated to 50° C. and charged with 22.54 parts of Reactant "B" and 3.14 parts of sodium hydroxide. This mixture was heated to 90°–95° C. and held within this temperature range until completion. The reaction was considered complete when theoretical inorganic chloride was generated.

EXAMPLE 86

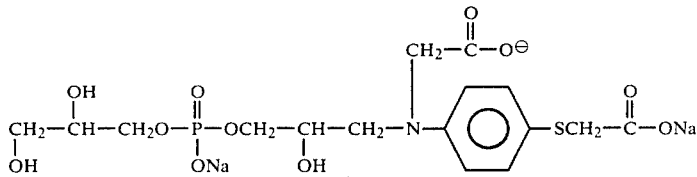

To 16.94 parts of N-carboxymethyl p-aminophenyl-mercaptacetic acid, were charged 60.00 parts of soft water in a reactor under good agitation. The reaction mixture was heated to 50° C. and charged with 20.24 parts of Reactant "B" and 2.82 parts sodium hydroxide. This mixture was heated to 90°–95° C. and held within this temperature range until completion. The reaction was considered complete when theoretical inorganic chloride was generated.

EXAMPLE 87

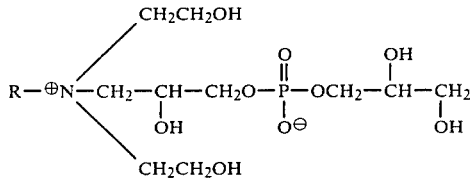

To 22.08 parts if molten bis-(2-hydroxyethyl)octadecyl amine, were charged 60.00 parts of water in a reactor under good agitation. The reaction mixture was heated to 70° C. and charged with 17.92 parts of Reactant "B". This mixture was heated to 90°–95° C. and held within this temperature range until completion. The reaction was considered complete when theoretical inorganic chloride was generated.
R=C₁₈

EXAMPLE 88

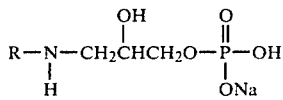

To 13.56 parts of n-octylamine were charged 60.00 parts of soft water in a reactor under good agitation. The reaction mixture was heated to 50° C. and charged with 22.26 parts of Reactant "A" and 4.2 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R=$C_8$

EXAMPLE 89

$$R-\underset{\underset{H}{|}}{N}-CH_2CHCH_2O-\underset{\underset{ONa}{|}}{\overset{\overset{O}{\|}}{P}}-OH$$
(with OH on the middle carbon)

To 16.94 parts of n-dodecylamine, were charged 60.00 parts of soft water in a reactor under good agitation. The reaction mixture was heated to 50° C. and charged with 19.40 parts of Reactant "A" and 3.66 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R=$C_{12}$

EXAMPLE 90

$$R-\underset{\underset{H}{|}}{N}-CH_2CHCH_2O-\underset{\underset{ONa}{|}}{\overset{\overset{O}{\|}}{P}}-OH$$
(with OH on middle carbon)

To 20.65 parts of n-octadecylamine, were charged 60.00 parts of soft water in a reactor under good agitation. The reaction mixture was heated to 50° C. and charged with 16.28 parts of Reactant "A" and 3.07 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R=$C_{18}$

EXAMPLE 91

$$R-\underset{\underset{H}{|}}{N}\ CH_2CHCH_2O-\underset{\underset{OH}{|}}{\overset{\overset{O}{\|}}{P}}-ONa$$

To 19.55 parts of n-hexadecylamine were charged 60.00 parts of soft water in a reactor under good agitation. The reaction mixture was heated to 50° C. and charged with 17.21 parts of Reactant "A" and 3.24 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R=$C_{16}$

EXAMPLE 92

$$R-\underset{\underset{H}{|}}{N}-CH_2CHCH_2O-\underset{\underset{ONa}{|}}{\overset{\overset{O}{\|}}{P}}-OCH_2CHCH_2$$
(with OH groups)

To 11.34 parts of n-octylamine were charged 60.00 parts of soft water in a reactor under good agitation. The reaction mixture was heated to 50° C. and charged with 25.14 parts of Reactant "B" and 3.52 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R=$C_8$

EXAMPLE 93

$$R-\underset{\underset{H}{|}}{N}-CH_2CHCH_2O-\underset{\underset{ONa}{|}}{\overset{\overset{O}{\|}}{P}}-OCH_2CHCH_2$$
(with OH groups)

To 14.48 parts of n-dodecylamine, were charged 60.00 parts of soft water in a reactor under good agitation. The reaction mixture was heated to 50° C. and charged with 22.39 parts of Reactant "B" and 3.13 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R=$C_{12}$

EXAMPLE 94

$$R-\underset{\underset{H}{|}}{N}-CH_2CHCH_2O-\underset{\underset{ONa}{|}}{\overset{\overset{O}{\|}}{P}}-OCH_2CHCH_2$$
(with OH, OH/OH groups)

To 18.08 parts of n-octadecylamine, were charged 60.00 parts of soft water in a reactor under good agitation. The reaction mixture was heated to 50° C. and charged with 19.23 parts of Reactant "B" and 2.69 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R=$C_{18}$

EXAMPLE 95

$$R-\underset{\underset{H}{|}}{N}-CH_2CHCH_2O-\underset{\underset{ONa}{|}}{\overset{\overset{O}{\|}}{P}}-OCH_2CHCH_2$$
(with OH, OH/OH groups)

To 17.10 parts of n-hexadecylamine were charged 60.00 parts of soft water in a reactor under good agitation. The reaction mixture was heated to 50° C. and charged with 20.18 parts of Reactant "B" and 2.82 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R=C$_{16}$

EXAMPLE 96

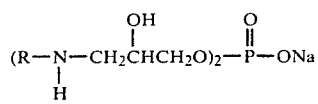

To 14.23 parts of n-octylamine were charged 60.00 parts of soft water in a reactor under good agitation. The reaction mixture was heated to 50° C. and charged with 21.36 parts of Reactant "D" and 4.41 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R=C$_8$

EXAMPLE 97

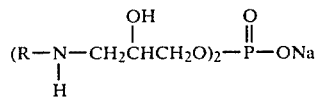

To 17.68 parts of n-didodecylamine were charged 60.00 parts of soft water in a reactor under good agitation. The reaction mixture was heated to 50° C. and charged with 18.50 parts of Reactant "D" and 3.82 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R=C$_{12}$

EXAMPLE 98

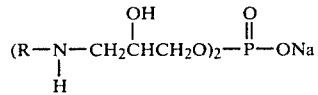

To 21.41 parts of n-octadecylamine were charged 60.00 parts of soft water in a reactor under good agitation. The reaction mixture was heated to 50° C. and charged with 15.50 parts of Reactant "D" and 3.09 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R=C$_{18}$

EXAMPLE 99

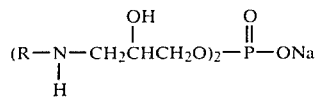

To 20.32 parts of n-hexadecylamine were charged 60.00 parts of soft water in a reactor under good agitation. The reaction mixture was heated to 50° C. and charged with 16.31 parts of Reactant "D" and 3.37 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R=C$_{16}$

EXAMPLE 100

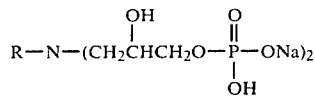

To 13.65 parts of n-octadecylamine were charged 60.00 parts of soft water in a reactor under good agitation. The reaction mixture was heated to 50° C. and charged with 21.94 parts of Reactant "A" and 4.14 parts of sodium hydroxide. This mixture was heated to 90°–95° C. and held within this temperature range until completed. The reaction was considered complete when theoretical inorganic chloride was generated.

The product is an aqueous solution having the general structure illustrated above.

R=C$_{18}$

EXAMPLE 101

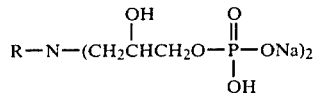

To 12.93 parts of n-hexadecylamine were charged 60.00 parts of soft water in a reactor under good agitation. The reaction mixture was heated to 50° C. and charged with 22.77 parts of Reactant "A" and 4.30 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R=C$_{16}$

EXAMPLE 102

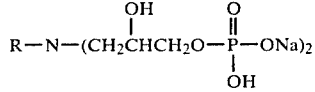

To 8.15 parts of n-octadecylamine were charged 60.00 parts of soft water in a reactor under good agitation. The reaction mixture was heated to 50° C. and charged with 26.79 parts of Reactant "A" and 5.06 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R=C$_{18}$

EXAMPLE 103

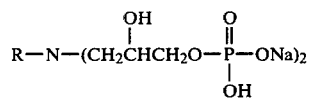

To 10.74 parts of n-dodecylamine were charged 60.00 parts of soft water in a reactor under good agitation. The reaction mixture was heated to 50° C. and charged with 24.62 parts of Reactant "A" and 4.64 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R=C$_{12}$

EXAMPLE 104

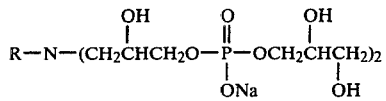

To 6.61 parts of n-octylamine were charged 60.00 parts of soft water in a reactor under good agitation. The reaction mixture was heated to 50° C. and charged with 29.30 parts of Reactant "B" and 4.09 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R=C$_8$

EXAMPLE 105

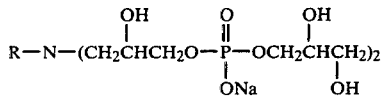

To 5.84 parts of n-dodecylamine were charged 60.00 parts of soft water in a reactor under good agitation. The reaction mixture was heated to 50° C. and charged with 27.34 parts of Reactant "B" and 3.82 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R=C$_{12}$

EXAMPLE 106

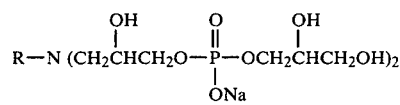

To 11.68 parts of n-octadecylamine were charged 60.00 parts of soft water in a reactor under good agitation. The reaction mixture was heated to 50° C. and charged with 24.84 parts of Reactant "B" and 3.48 parts of sodium hydroxide. This mixture was heated to 90°–95° C. and held within this temperature range until completion. The reaction was considered complete when theoretical inorganic chloride was generated.

The product is an aqueous solution having the general formula structure illustrated above.

R=C$_{18}$

EXAMPLE 107

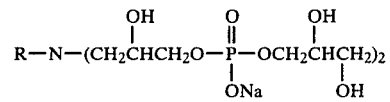

To 10.80 parts of n-hexadecylamine were charged 60.00 parts of soft water in a reactor under good agitation. The reaction mixture was heated to 50° C. and charged with 25.62 parts of Reactant "B" and 3.58 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R=C$_{16}$

EXAMPLE 108

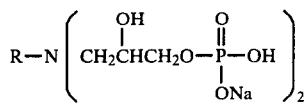

To 8.45 parts of n-octylamine were charged 60.00 parts of soft water in a reactor under good agitation. The reaction mixture was heated to 50° C. and charged with 26.32 parts of Reactant "C" and 5.23 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R=C$_8$

EXAMPLE 109

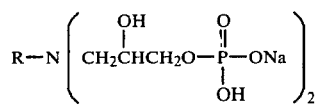

To 14.33 parts of n-octadecylamine were charged 60.00 parts of soft water in a reactor under good agitation. The reaction mixture was heated to 50° C. and charged with 21.41 parts of Reactant "C" and 4.26 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R = C$_{18}$

EXAMPLE 110

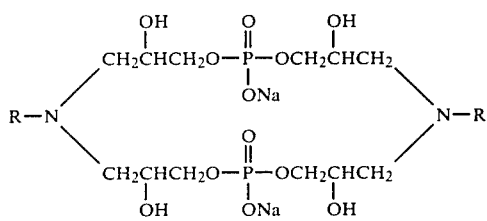

To 8.66 parts of n-octylamine were charged 60.00 parts of soft water in a reactor under good agitation. The reaction mixture was heated to 50° C. and charged with 25.97 parts of Reactant "D" and 5.37 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R = C$_8$

EXAMPLE 111

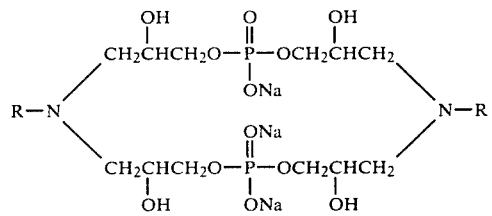

To 11.35 parts of n-dodecylamine were charged 60.00 parts of soft water in a reactor under good agitation. The reaction mixture was heated to 50° C. and charged with 23.74 parts of Reactant "D" and 4.91 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R = C$_{12}$

EXAMPLE 112

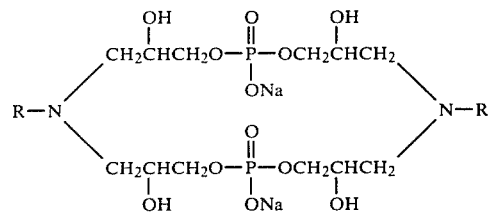

To 14.62 parts of n-octadecylamine were charged 60.00 parts of soft water in a reactor under good agitation. The reaction mixture was heated to 50° C. and charged with 21.03 parts of Reactant "D" and 4.35 parts of sodium hydroxide. This mixture was heated to 90°–95° C. and held within this temperature range until completed. The reaction was considered complete when theoretical inorganic chloride was generated.

The product is an aqueous solution having the general structure illustrated above.

R = C$_{18}$

EXAMPLE 113

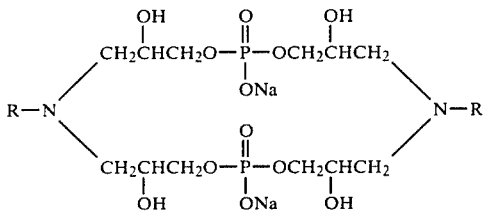

To 13.62 parts of n-hexylamine were charged 60.00 parts of soft water in a reactor under good agitation. The reaction mixture was heated to 50° C. and charged with 21.86 parts of Reactant "D" and 4.70 parts of sodium hydroxide. This mixture was heated to 90°–95° C. and held within this temperature range until completion. The reaction was considered complete when the theoretical inorganic chloride was generated.

The product is an aqueous solution having the general structure illustrated above.

R = C$_6$

EXAMPLE 114

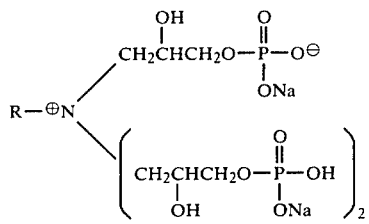

To 6.11 parts of N-octylamine were charged 60.00 parts of soft water in a reactor under good agitation. The reaction mixture was heated to 50° C. and charged with 30.11 parts of Reactant "A" and 3.78 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R = C$_8$

EXAMPLE 115

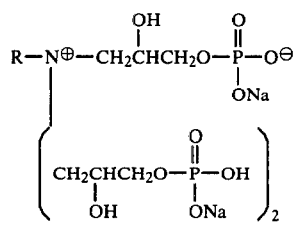

To 8.21 parts of n-dodecylamine were charged 60.00 parts of soft water in a reactor under good agitation. The reaction mixture was heated at 50° C. and charged with 28.24 parts of Reactant "A" and 3.55 parts of sodium hydroxide. This mixture was heated to 90°-95° C. and held within this temperature range until completion. The reaction was considered complete when theoretical inorganic chloride was generated.

The product is an aqueous solution having the general formula illustrated above.

R=C$_{12}$

EXAMPLE 116

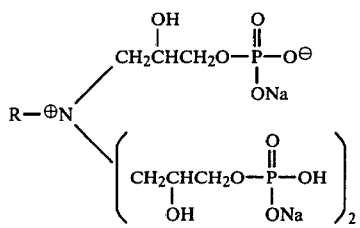

To 10.92 parts of n-octadecylamine were charged 60.00 parts of soft water in a reactor under good agitation. The reaction mixture was heated to 50° C. and charged with 25.83 parts of Reactant "A" and 3.25 parts of sodium hydroxide. This mixture was heated to 90°-95° C. and held within this temperature range until completion. The reaction was considered complete when theoretical inorganic chloride was generated.

The product is an aqueous solution having the general structure illustrated above.

R=C$_{18}$

EXAMPLE 117

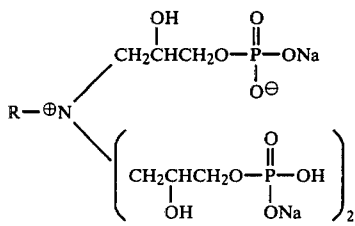

To 10.07 parts of hexadecylamine were charged 60.00 parts of soft water in a reactor under good agitation. The reaction mixture was heated to 50° C. and charged with 24.58 parts of Reactant "A" and 5.35 parts of sodium hydroxide. This mixture was heated to 90°-95° C. and held within this temperature range until completion. The reaction was considered complete when theoretical inorganic chloride was generated.

The product is an aqueous solution having the general structure illustrated above.

R=C$_{16}$

EXAMPLE 118

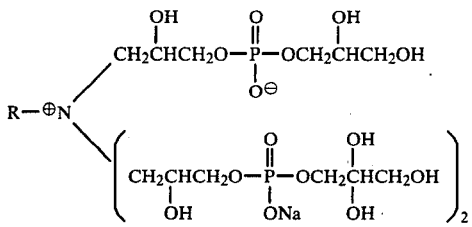

To 4.84 parts of n-octylamine were charged 60.00 parts of soft water in a reactor under good agitation. The reaction mixture was heated to 50° C. and charged with 32.16 parts of Reactant "B" and 3.00 parts of sodium hydroxide. This mixture was heated to 90°-95° C. and held within this temperature range until completion. The reaction was considered complete when theoretical inorganic chloride was generated.

The product is an aqueous solution having the general structure illustrated above.

R=C$_8$

EXAMPLE 119

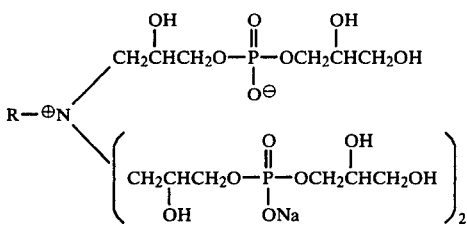

To 6.59 parts of n-dodecylamine were charged 60.00 parts of soft water in a reactor under good agitation. The reaction mixture was heated to 50° C. and charged with 30.56 of Reactant "B" and 2.85 parts of sodium hydroxide. This mixture was heated to 90°-95° C. and held within this temperature range until completion. The reaction was considered complete when theoretical inorganic chloride was generated.

The product is an aqueous solution having the general structure illustrated above.

R=C$_{12}$

EXAMPLE 120

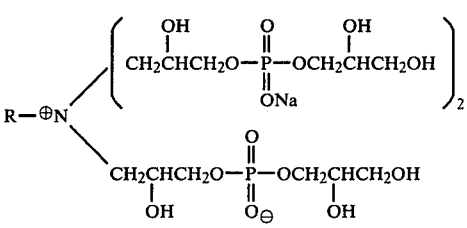

To 8.91 parts of Octadecylamine were charged 60.00 parts of soft water in a reactor under good agitation. The reaction mixture was heated to 50° C. and charged with 28.43 parts of Reactant "B" and 2.66 parts of sodium hydroxide. This mixture was heated to 90°-95° C.

and held within this temperature range until completion. The reaction was considered complete when theoretical inorganic chloride was generated.

The product is an aqueous solution having the general structure illustrated above.

R = C$_{18}$

EXAMPLE 121

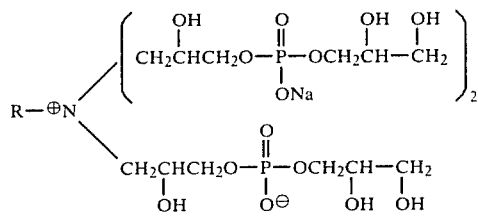

To 8.18 parts of n-hexadecylamine were charged to 60.00 parts of soft water in a reactor under good agitation. The reaction mixture was heated to 50° C. and charged with 29.11 parts of Reactant "B" and 2.71 parts of sodium hydroxide. This mixture was heated to 90°-95° C. and held within this temperature range until completion. The reaction was considered complete when theoretical inorganic chloride was generated.

The product is an aqueous solution having the general structure illustrated above.

R = C$_{16}$

EXAMPLE 122

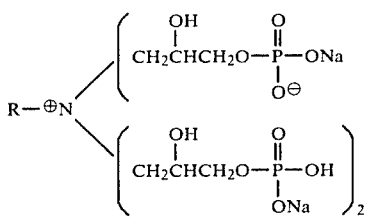

To 6.35 parts of n-octylamine were charged 60.00 parts of soft water in a reactor under good agitation. The reaction mixture was heated to 50° C. and charged with 29.70 parts of Reactant "C" and 3.95 parts of sodium hydroxide. This mixture was heated to 90°-95° C. and held within this temperature range until completion. Reaction was considered complete when theoretical inorganic chloride was generated.

The product is an aqueous solution having the general structure illustrated above.

R = 8.

EXAMPLE 123

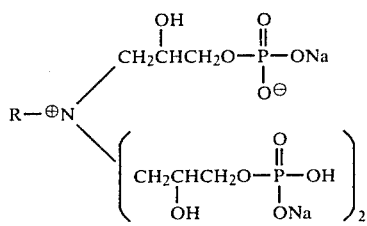

To 11.30 parts of didecylamine were charged 60.00 parts of soft water in a reactor under good agitation. The reaction mixture was heated to 50° C. and charged with 25.34 parts of Reactant "C" and 3.36 parts of sodium hydroxide. This mixture was heated to 90°-95° C. and held within this temperature range until completion. The reaction was considered complete when theoretical inorganic chloride was generated.

The product is an aqueous solution having the general structure illustrated above.

R = 10

EXAMPLE 124

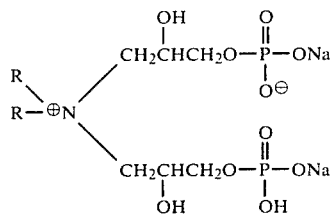

To 18.75 parts of n-dicocoamine were charged 60.00 parts of soft water in a reactor under good agitation. The reaction mixture was heated to 50° C. and charged with 19.33 parts of Reactant "C" and 1.92 parts of sodium hydroxide. This mixture was heated to 90°-95° C. and held within this temperature range until completion. The reaction was considered complete when theoretical inorganic chloride was generated.

The product is an aqueous solution having the general structure illustrated above.

R = C$_8$ to C$_{18}$

EXAMPLE 125

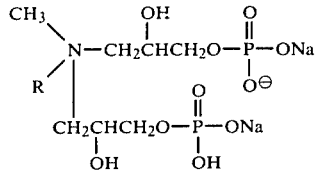

To 12.24 parts of N-methyl-N-laurylamine were charged 60.00 parts of soft water in a reactor under good agitation. The reaction mixture was heated to 50° C. and charged with 25.24 parts of Reactant "C" and 2.52 parts of sodium hydroxide. This mixture was heated to 90°-95° C. and held within this temperature range until completion. The reaction is considered complete when theoretical inorganic chloride was generated.

The product is an aqueous solution having the general structure illustrated above.

R = C$_{12}$

EXAMPLE 126

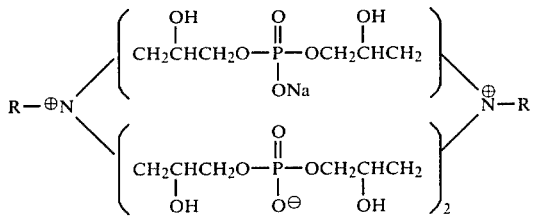

To 6.51 parts of n-octylamine were charged 60.00 parts of soft water in a reactor. The reaction mixture was heated to 50° C. and charged with 29.41 parts of Reactant "D" and 4.04 parts of sodium hydroxide. This mixture was heated to 90°-95° c. and held within this temperature range until completion. The reaction was considered complete when theoretical inorganic chloride was generated.

The product is an aqueous solution having the general structure illustrated above.

R=$C_8$

EXAMPLE 127

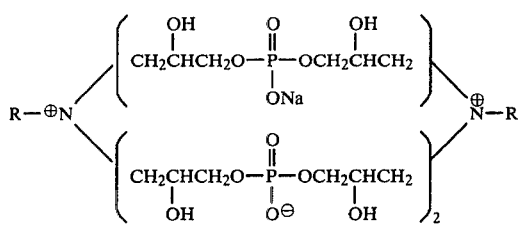

To 8.75 parts of n-dodecylamine were charged 60.00 parts of soft water in a reactor. The reaction mixture was heated to 50° C. and charged with 27.46 parts of Reactant "D" and 3.79 of sodium hydroxide. This mixture was heated to 90°-95° C. and held within this temperature range until completion. The reaction was considered complete when theoretical inorganic chloride was generated.

The product is an aqueous solution having the general structure illustrated above.

R=$C_{12}$

EXAMPLE 128

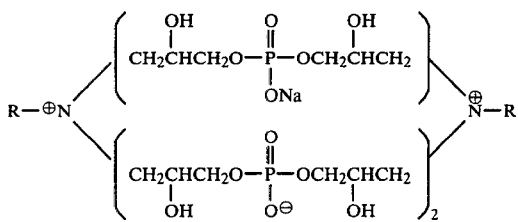

To 11.58 parts of n-octadecylamine was charged 60.00 parts of soft water in a reactor under good agitation. The reaction mixture was heated to 50° C. and charged with 25.50 parts of Reactant "D" and 3.42 parts of sodium hydroxide. This mixture was heated to 90°-95° C. and held within this temperature range until completion. The reaction was considered complete when theoretical inorganic chloride was generated.

The product is an aqueous solution having the general structure illustrated above.

R=$C_{18}$

EXAMPLE 129

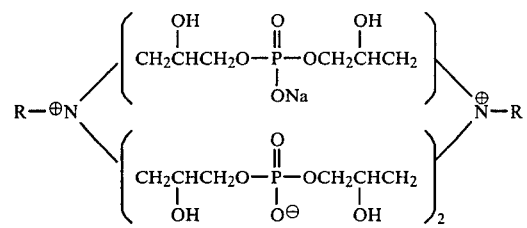

To 10.69 parts of n-hexadecylamine were charged 60.00 parts of soft water in a reactor under good agitation. The reaction mixture was heated to 50° C. and charged with 25.76 parts of Reactant "D" and 3.55 parts of sodium hydroxide. This mixture was heated to 90°-95° C. and held within this temperature range until completion. The reaction was considered complete when theoretical inorganic chloride was generated.

The product is an aqueous solution having the general structure illustrated below.

R=$C_{16}$

EXAMPLE 130

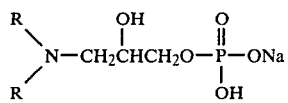

To 24.30 parts of dicocoamine were charged 60.00 parts of soft water in a reactor under good agitation. The reaction mixture was heated to 50° C. and charged with 13.21 parts of Reactant "A" and 2.49 parts of sodium hydroxide. This mixture was heated to 90°-95° C. and held within this temperature range until completion. The reaction was considered complete when theoretical inorganic chloride was generated.

The product is an aqueous solution having the general structure illustrated above.

R=$C_8$ to $C_{18}$

EXAMPLE 131

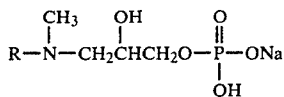

To 17.45 parts of N-methyl-N-laurylamine were charged 60.00 parts of soft water in a reactor under good agitation. The reaction mixture was heated to 50° C. and charged with 18.97 parts of Reactant "A" and 3.58 of sodium hydroxide. This mixture was heated to 90°-95° C. and held within this temperature range until completion. The reaction was considered complete when theoretical inorganic chloride was generated.

The product is an aqueous solution having the general structure illustrated above.

R=$C_{12}$

EXAMPLE 132

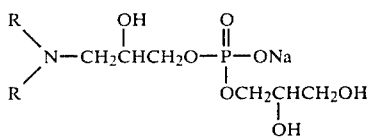

To 21.79 parts of dicocoamine were charged 60.00 parts of soft water in a reactor under good agitation. The reaction mixture was heated to 50° C. and charged with 15.98 parts of Reactant "B" and 2.23 of sodium hydroxide. This mixture was heated to 90°–95° C. and held within this temperature range until completion. The reaction was considered complete when theoretical inorganic chloride was generated.

The product is an aqueous solution having the general structure illustrated above.

EXAMPLE 133

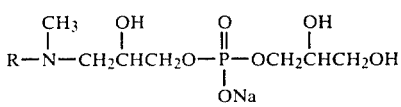

To 14.97 parts of N-methyl-N-laurylamine were charged 60.00 parts of soft water in a reactor under good agitation. The reaction mixture was heated to 50° C. and charged with 21.97 parts of Reactant "B" and 3.06 parts of sodium hydroxide. This mixture was heated to 90°–95° C. and held within this temperature range until completion. The reaction was considered complete when theoretical inorganic chloride was generated.

The product is an aqueous solution having the general structure illustrated above.

EXAMPLE 134

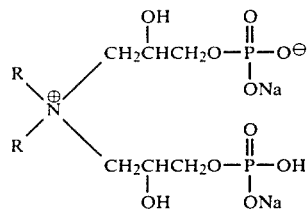

To 24.72 parts of N-dicocoamine were charged 60.00 parts of soft water in a reactor under good agitation. The reaction mixture was heated to 50° C. and charged with 12.74 parts of reactant "C" and 2.54 parts of sodium hydroxide. This mixture was heated to 90°–95° C. and held within this temperature range until completion. The reaction was considered complete when theoretical inorganic chloride was generated.

The product is an aqueous solution of the general structure illustrated above.

R=C$_{8-18}$

EXAMPLE 135

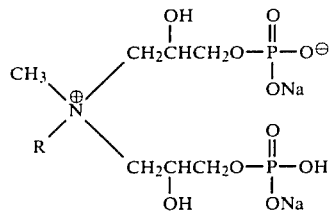

To 17.89 parts of N-methyl-N-laurylamine were charged 60.00 parts of soft water in a reactor under good agitation. The reaction mixture was heated to 50° C. and charged with 18.44 parts of Reactant "C" and 3.67 sodium hydroxide. This mixture was heated to 90°–95° C. and held within this temperature range until completion. The reactant was considered complete when theoretical inorganic chloride was generated.

The product is an aqueous solution having the general structure illustrated above.

R = 12

EXAMPLE 136

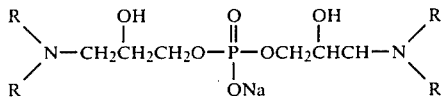

To 19.10 parts of dicocoamine were charged 60.00 parts of soft water in a reactor under good agitation. The reaction mixture was heated to 50° C. and charged with 18.95 parts of Reactant "D" and 1.95 sodium hydroxide. This mixture was heated to 90°–95° C. and held within this temperature range until completion. The reaction was considered complete when theoretical inorganic chloride was generated.

The product is an aqueous solution having the general structure illustrated above.

R=C$_8$ to C$_{18}$

EXAMPLE 137

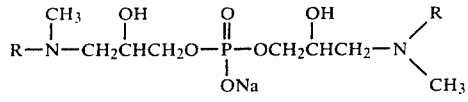

To 12.54 parts of N-methyl-N-laurylamine were charged 60.00 parts of soft water in a reactor under good agitation. The reaction mixture was heated to 50° C. and charged with 24.89 parts of Reactant "D" and 2.51 parts of sodium hydroxide. This mixture was heated to 90°–95° C. and held within this temperature range until completion. The reaction was considered complete when theoretical inorganic chloride was generated.

The product is an aqueous solution having the general structure illustrated above.

R=C$_{12}$

EXAMPLE 138

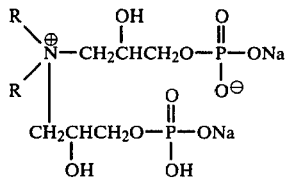

To 18.27 parts of dicocoamine were charged 60.00 parts of soft water in a reactor under good agitation. The reaction mixture was heated to 50° C. and charged with 19.86 parts of Reactant "A" and 1.86 parts of sodium hydroxide. This mixture was heated to 90°-95° C. and held within this temperature range until completion. The reaction was considered complete when theoretical inorganic chloride was generated.

The product is an aqueous solution having the general structure illustrated above.

R = $C_8$ to $C_{18}$

EXAMPLE 139

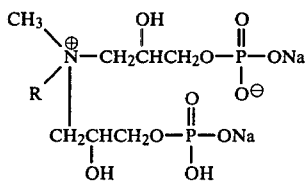

To 11.84 parts of N-methyl-N-laurylamine were charged 60.00 parts of soft water in a reactor under good agitation. The reaction mixture was heated to 50° C. and charged with 25.74 parts of Reactant "A" and 2.42 parts of sodium hydroxide. This mixture was heated to 90°-95° C. and held within this temperature range until completion. The reaction was considered complete when theoretical inorganic chloride was generated.

The product is an aqueous solution having the general structure illustrated above.

R = $C_{12}$

EXAMPLE 140

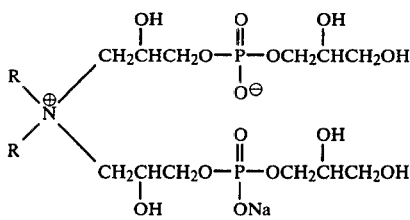

To 15.57 parts of dicocoamine were charged 60.00 parts of soft water in a reactor under good agitation. The reaction mixture was heated to 50° C. and charged with 22.83 parts of Reactant "B" and 1.60 parts of sodium hydroxide. This mixture was heated to 90°-95° C. and held within this temperature range until completion. The reaction was considered complete when theoretical inorganic chloride was generated.

The product is an aqueous solution having the general structure illustrated above.

R = $C_{8-18}$.

EXAMPLE 141

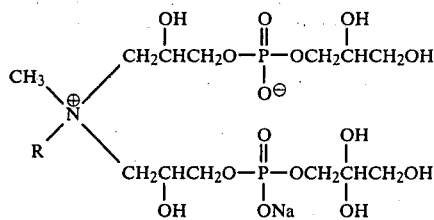

To 9.67 parts of N-methyl-N-laurylamine were charged 60.00 parts of soft water in a reactor under good agitation. The reaction mixture was heated to 50° C. and charged with 28.35 parts Reactant "B" and 1.98 parts of sodium hydroxide. This mixture was heated to 90°-95° C. and held within this temperature range until completion. The reaction was considered complete when theoretical inorganic chloride was generated.

The product is an aqueous solution having the general structure illustrated above.

R = $C_{12}$

EXAMPLE 142

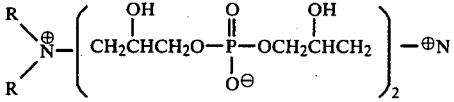

To 15.49 parts of dicocoamine were charged 60.00 parts of soft water in a reactor under good agitation. The reaction mixture was heated to 50° C. and charged with 18.95 parts of Reactant "D" and 5.56 parts of sodium hydroxide. The mixture was heated to 90°-95° C. and held within this temperature range until completion. The reaction was considered complete when theoretical inorganic chloride was generated.

The product is an aqueous solution having the general structure illustrated above.

R = $C_8$ to $C_{18}$

EXAMPLE 143

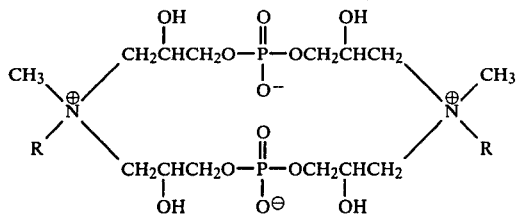

To 12.54 parts of N-methyl-N-laurylamine were charged 60.00 parts of soft water in a reactor under good agitation. The reaction mixture was heated to 50° C. and charged with 24.89 parts of Reactant "D" and 2.57 parts of sodium hydroxide. This mixture was heated to 90°-95° C. and held within this temperature range until completion. The reaction was considered complete when theoretical inorganic chloride was generated.

The product is an aqueous solution having the general structure illustrated above.

R = $C_{12}$

EXAMPLE 144

28.05 parts of Reactant "B" and 60.0 parts water were charged into a suitable reaction vessel under good agitation. Heat was applied to 50° C. 11.95 parts of N, N-dimethylbenzylamine were charged under good agitation. Heating was continued to 90°-95° C. and held at this temperature for 4 hours. The reaction reached 97% during this time via inorganic chloride and tertiary amine analysis.

The product is an aqueous solution of a novel product having the following structure:

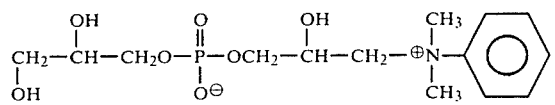

EXAMPLE 145

29.35 parts of Reactant "B" and 60.0 parts water were charged into a suitable reaction vessel under good agitation. Heat was applied to 50° C. 10.65 parts of N-ethylmorpholine were charged under good agitation. Heating was continued to 90°-95° C. and held at this temperature for 4 hours. The reaction reached 97% during this time via inorganic chloride and tertiary amine analysis.

The product is an aqueous solution of a novel product having the following structure:

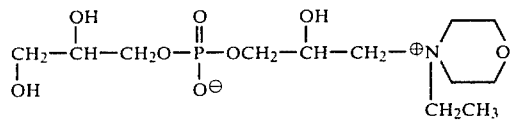

EXAMPLE 146

26.35 parts of Reactant "D" and 60.0 parts water were charged into a suitable reaction vessel under good agitation. 13.65 parts parts of alkyldimethylamine (alkyl being $C_{12}$) were charged under good agitation. Heating was continued to 90°-95° C. and held at this temperature for 4 hours. Reaction reached 97% during this time via inorganic chloride and tertiary amine analysis.

The product is an aqueous solution of one of the novel products having the following structure:

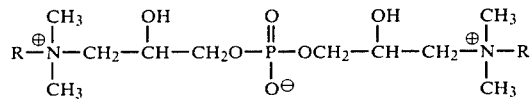

$R = C_{12}$

EXAMPLE 147

25.25 parts of Reactant "D" and 60.0 parts water were charged into a suitable reaction vessel under good agitation. Heat was applied to 50° C. 14.75 parts of alkyldimethylamine (alkyl being $C_{14}$) were charged under good agitation. Heating was continued to 90°-95° C. and held at this temperature for 4 hours. Reaction reached 97% during this time via inorganic chloride and tertiary amine analysis.

The product is an aqueous solution of one of the novel products having the following structure:

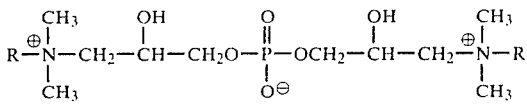

$R = C_{14}$

EXAMPLE 148

25.8 parts of Reactant "B" and 60.0 parts water were charged into a suitable reaction vessel under good agitation. Heat was applied to 50° C. 14.2 parts of alkyldimethylamine (alkyl being $C_{12}$) were charged under good agitation. Heating was continued to 90°-95° C. and held at this temperature for 4 hours. Reaction reached 97% during this time via inorganic chloride and tertiary amine analysis.

The product is an aqueous solution of one of the novel products having the following structure:

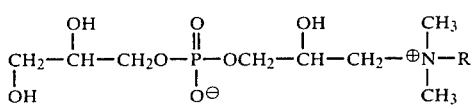

$R = C_{12}$

EXAMPLE 149

24.7 parts of Reactant "B" and 60.0 parts water were charged into a suitable reaction vessel under good agitation. Heat was applied to 50° C. 15.3 parts of alkyldimethylamine (alkyl being $C_{16}$) were charged under good agitation. Heating was continued to 90°-95° C. and held at this temperature for 4 hours. Reaction reached 97% during this time via inorganic chloride and tertiary amine analysis.

The product is an aqueous solution of one of the novel products having the following structure:

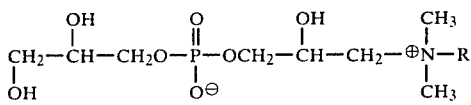

$R = C_{16}$

EXAMPLE 150

23.8 parts of Reactant "A" and 60.0 parts water were charged into a suitable reaction vessel under good agitation. Heat was applied to 50° C. 17.46 parts of alkyldimehtylamine (alkyl being $C_{14}$) were charged under good agitation. Heating was continued to 90°-95° C. and held at this temperature for 4 hours. Reaction reached 97% during this time via inorganic chloride and tertiary amine analysis.

The product is an aqueous solution of one of the novel products having the following structure:

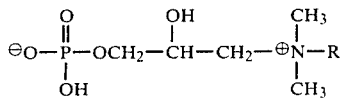

$R = C_{14}$

EXAMPLE 151

22.54 parts of Reactant "A" and 60.0 parts water were charged into a suitable reaction vessel under good agitation. Heat was applied to 50° C. 17.46 parts of alkyldimethylamine (alkyl being $C_{14}$) were charged under good agitation. Heating is continued to 90°–95° C. and held at this temperature for 4 hours. Reaction reached 97% during this time via inorganic chloride and tertiary amine analysis.

The product is an aqueous solution of one of the novel products having the following structure:

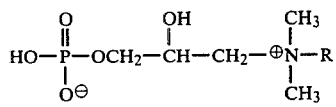

$R = C_{14}$

EXAMPLE 152

24.67 parts of Reactant "C" and 60.0 parts water were charged into a suitable reaction vessel under good agitation. Heat was applied to 50° C. 15.33 parts of alkyldimethylamine (alkyl being $C_{12}$) were charged under good agitation. Heating was continued to 90°–95° C. and held at this temperature for 4 hours. Reaction reached 97% during this time via inorganic chloride and tertiary amine analysis.

The product is an aqueous solution of one of the novel products having the following structure:

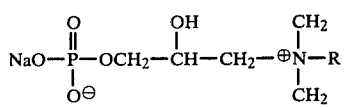

$R = C_{12}$

EXAMPLE 153

23.52 parts of Reactant "C" and 60.0 parts water were charged into a suitable reaction vessel under good agitation. Heat was applied to 50° C. 16.48 parts of alkyldimethylamine (alkyl being $C_{14}$) were charged under good agitation. Heating was continued to 90°–95° C. and held at this temperature for 4 hours. Reaction reached 97% during this time via inorganic chloride and tertiary amine analysis.

The product is an aqueous solution of one of the novel products having the following structure:

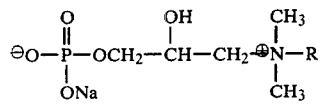

$R = C_{14}$

EXAMPLE 154

22.47 parts of Reactant "C" and 60.0 parts water were charged into a suitable reaction vessel under good agitation. Heat was applied to 50° C. 17.53 parts of alkyldimethylamine (alkyl being $C_{16}$) were charged under good agitation. Heating was continued to 90°–95° C. and held at this temperature for 4 hours. Reaction reached 97% during this time via inorganic chloride and tertiary amine analysis.

The product is an aqueous solution of one of the novel products having the following structure:

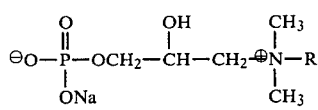

$R = C_{16}$

EXAMPLE 155

21.51 parts of Reactant "C" and 60.0 parts water were charged into a suitable reaction vessel under good agitation. Heat was applied to 50° C. 18.49 parts of alkyldimethylamine (alkyl being $C_{18}$) were charged under good agitation. Heating was continued to 90°–95° C. and held at this temperature for 4 hours. Reaction reached 97% during this time via inorganic chloride and tertiary amine analysis.

The product is an aqueous solution of one of the novel prodcuts having the following structure:

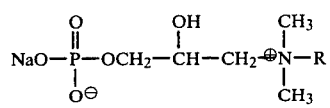

$R = C_{18}$

EXAMPLE 156  REACTANT "A"

60.00 parts of deionized water are charged into a suitable reactor to which 22.58 parts of $NaH_2PO_4$ and 0.70 parts of NaOH are charged under good agitation. Mix well until a solution is obtained. 17.42 parts of Epichlorohydrin is charged under good agitation. The reactor is sealed and 5 PSIG $N_2$ is applied. Heat to 80°–85° C. holding the heated mixture at this temperature for 2 hours after the batch clears (approximately 3 hours total). Reaction is complete when theoretical reduction in acid value is obtained. Inorganic chloride will be less than 0.50%.

The product is an aqueous solution of a novel product having the following structure:

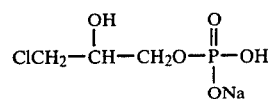

EXAMPLE 157  REACTANT "B"

60.00 parts of deionized water are charged into a suitable reactor to which 17.37 parts of $Na_2HPO_4$ are charged. Mix well until a solution is obtained. 22.63 parts of Epichlorohydrin are charged under good agitation. The reactor is sealed and 5 PSIG $N_2$ is applied. Heat to 80°–85° C. holding the heated mixture at this temperature for approximately 2 hours after the batch clears (approximately 3 hours total). Reaction is complete when theoretical chloride is obtained and theoretical reduction in acid value is realized.

The product is an aqueous solution of a novel product having the following structure:

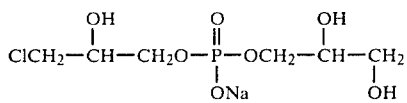

EXAMPLE 158 REACTANT "C"

60.00 parts of deionized water are charged into a suitable reactor to which 17.37 parts of Na$_2$HPO$_4$ are charged. Mix well until a solution is obtained. 22.63 parts of Epichlorohydrin are charged under good agitation. The reactor is sealed and 5 PSIG N$_2$ is applied. Heat to 80°–85° C. holding the heated mixture at this temperature for 2 hours after the batch clears (approximately 3 hours total). Reaction is complete when theoretical reduction in acid value and theoretical inorganic chloride values are obtained.

The product is an aqueous solution of a novel product having the following structure:

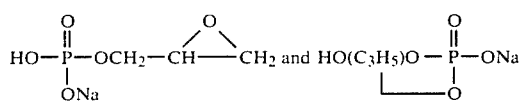

EXAMPLE 159 REACTANT "D"

60.00 parts of deionized water are charged into a suitable reactor to which 17.09 parts of NaH$_2$PO$_4$ and 0.70 parts of NaOH are charged. Mix well until a solution is achieved. 22.91 parts of Epichlorohydrin is charged under good agitation. Reactor is sealed and 5 PSIG N$_2$ is applied. Heat is applied to approximately 80°–85° C. and the heated mixture held at this temperature for approximately 3 hours after the batch clears (approximately 5 hours total). Reaction is complete when acid value is reduced by the theoretical amount. Inorganic chloride will be less than 0.5%

The product is an aqueous solution of a novel product having the following structure:

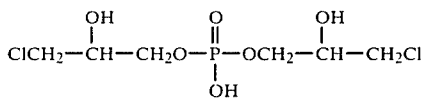

EXAMPLE 160 REACTANT "E"

48.79 parts of 2-chloroethanol is slowly charged into 51.21 parts of polyphosphoric acid under good agitation. The mixture is slowly heated to 90°–95° C. and held at this temperature for approximately 2 hours. Reaction is complete when theoretical reduction in acid value is obtained. 35.67 parts of the above product are mixed with 55.14 parts of deionized water. 8.32 parts of NaOH is slowly charged. Reaction is complete when theoretical acid value is obtained.

The product is an aqueous solution of a novel product having the following structure:

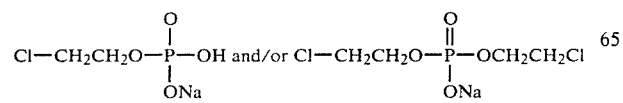

EXAMPLE 161 REACTANTS "I"

66.17 parts of 1-chloro-2-propanol are slowly charged to 33.83 parts of polyphosphoric acid under good agitation. Heat slowly to 90°–95° C. holding the heated mixture at this temperature for approximately 2 hours. Reaction is complete when theoretical reduction in acid value is obtained. 34.90 parts of the above are mixed with 60.00 parts soft water. 5.10 parts NaOH are slowly added. Reaction is complete when theoretical reduction in acid value is achieved.

The product is an aqueous solution of a novel product having the following structure:

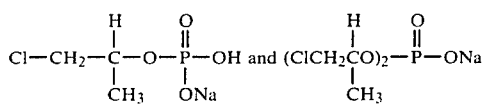

EXAMPLE 162 REACTANT "F"

69.60 parts of 2[2(2-chloroethoxy-ethoxy) ethanol are slowly charged to 30.40 parts of polyphosphoric acid under good agitation. Heat slowly to 90°–95° C. holding the heated mixture at this temperature for approximately 2 hours. Reaction is complete when theoretical reduction in acid value is obtained. 35.36 parts of the above are mixed with 60.00 parts soft water. 4.64 parts NaOH are slowly added. Reaction is complete when theoretical reduction in acid value is achieved.

The product is an aqueous solution of a novel product having the following structure:

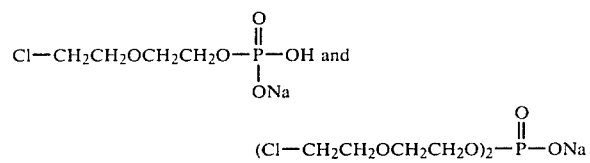

EXAMPLE 163 REACTANT "C"

68.09 parts of 3-chloro-1,2-propanediol are slowly charged to 31.91 parts of polyphosphoric acid under good agitation. Heat slowly to 90°–95° C. holding the heated mixture at this temperature for approximately 2 hours. Reaction is complete when theoretical reduction in acid value is obtained. 35.17 parts of the above are mixed with 60.00 parts soft water. 4.83 parts NaOH are slowly added. Reaction is complete when theoretical reduction in acid value is achieved.

The product is an aqueous solution of a novel product having the following structure:

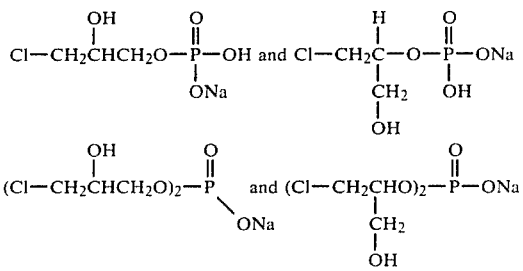

EXAMPLE 164 REACTANT "H"

66.17 parts of 1-chloro-3-hydroxy-propane are slowly charged to 33.83 parts of polyphosphoric acid under good agitation. Heat slowly to 90°–95° C. holding the heated mixture at this temperature for approximately 2 hours. Reaction is complete when theoretical reduction in acid value is obtained. 35.44 parts of the above are mixed with 60.00 parts soft water. 4.56 parts NaOH are slowly added. Reaction is complete when theoretical reduction in acid value is achieved.

The product is an aqueous solution of a novel product having the following structure:

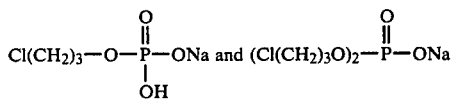

It will be understood that the specification and examples are illustrative but not limitative of the present invention and that other embodiments within the spirit and scope of the invention will suggest themselves to those skilled in the art.

What is claimed is:

1. Process for the production of phosphobetaine compounds, which process comprises reacting in aqueous medium a tertiary reactant of at least 6 carbon atoms, to produce an amphoteric phosphobetaine surfactant having at least one phosphorus-containing anion in the molecule, wherein said phosphate ester reactant is of the formula

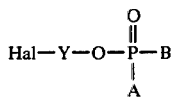

where
Hal is halogen
A is selected from $O^-$, OM, and $-O-Y-Hal$
B is selected from $O^-$ and $OM'$
with the proviso that only one of A and B can be $O^-$
Y may be alkylene, optionally interrupted by up to 3 oxygen atoms, of up to 12 carbon atoms, which alkylene chain may optionally be substituted with lower alkyl, alkoxy, hydroxy or hydroxyalkyl, e.g., of not more than 10 carbon atoms each;
M and M' are individually selected from (a) hydrogen, (b) an organic radical selected from alkyl or hydroxy-alkyl of up to 6 carbon atoms, polyhydroxyalkyl of up to 10 carbon atoms, glyceryl, cycloalkyl of up to 6 carbon atoms, aryl or arylalkyl of up to 10 carbon atoms, or (c) a salt radical selected from alkali metals, alkaline earth metals, and mono-, di-, or triethanolamine, with the proviso that when both M and M' are contained in said phosphate reactant and M or M' is an organic radical (b), the other of M and M' must be hydrogen or a salt radical (c).

2. Process as claimed in claim 1 wherein said amine reactant is of the formula

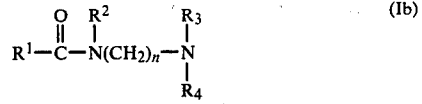

wherein
$R^1$ is alkyl, alkenyl, alkoxy, or hydroxyalkyl of from 5 to 22 carbon atoms each, or aryl or alkaryl of up to 20 carbon atoms,
$R^2$ is hydrogen or alkyl, hydroxyalkyl or alkenyl of up to 6 carbon atoms each or cycloalkyl of up to 6 carbon atoms, preferably of from 2 to 5 carbon atoms, or polyoxyalkalene of up to 10 carbon atoms,
$R^3$ and $R^4$, which may be the same or different, are selected from alkyl, hydroxyalkyl, carboxyalkyl of up to 6 carbon atoms in each alkyl moiety, and polyoxyalkylene of up to 10 carbon atoms; in addition, $R^3$ and $R^4$, taken together with the nitrogen to which they are attached, may represent an N-heterocycle in which the Y radical is bonded to a ring atom of said N-heterocycle other than the nitrogen of the amine moiety;
n is an integer from 2 to 12.

3. Process as claimed in claim 1 wherein said amine reactant is of the formula

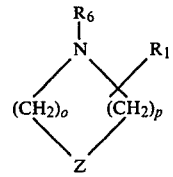

wherein
Z is N or O;
o is an integer from 0 to 3;
p is an integer from 1 to 3
provided that the sum of o+p is from 3 to 4;
$R^1$ is defined as before and is linked to a ring carbon atom; and
$R_6$ is alkyl of from 2 to 6 carbon atoms which may be substituted with a hydroxyl group at the terminal or a non-terminal carbon atom.

4. Process as claimed in claim 2 wherein said amine reactant is of the formula

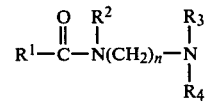

wherein
$R^1$ is alkyl, alkenyl, alkoxy, or hydroxyalkyl of from 5 to 22 carbon atoms each, or aryl or alkaryl of up to 20 carbon atoms,
$R^2$ is hydrogen or alkyl, hydroxyalkyl or alkenyl of up to 6 carbon atoms each or cycloalkyl of up to 6 carbon atoms, preferably of from 2 to 5 carbon atoms, or polyoxyalkalene of up to 10 carbon atoms, and
$R^4$ is selected from alkyl hydroxyalkyl, carboxyalkyl of up to 6 carbon atoms in each alkyl moiety, and polyoxyalkylene of up to 10 carbon atoms;
n is an integer from 2 to 12.

5. Process as claimed in claim 1 wherein the reaction is represented as follows:

$$R + Hal-Y-O-\underset{A}{\overset{\overset{O}{\|}}{P}}-B \quad (Ia)$$

$$(1) \downarrow -Hal \quad X_z^{\ominus}$$

$$\left[\overset{+}{R}-Y-O-\underset{A}{\overset{\overset{O}{\|}}{P}}-B\right] X_z^{\ominus} \quad (I)$$

wherein
Hal is halogen
A is selected from O⁻, OM, and —O—Y—Hal
B is selected from O⁻ and OM'
with the proviso that only one of A and B can be O⁻
Y may be alkylene, optionally interrrupted by up to 3 oxygen atoms, of up to 12 carbon atoms, which alkylene chain may optionally be substituted with lower alkyl, alkoxy, hydroxy or hydroxyalkyl of not more than 10 carbon atoms each;
R⁺ represents an amine moiety;
M and M', which may be the same or different, are
   (a) hydrogen,
   (b) an organic radical selected from alkyl or hydroxyalkyl of up to 6 carbon atoms, polyhydroxyalkyl of up to 10 carbon atoms, glyceryl, cycloalkyl of up to 6 carbon atoms, aryl or arylalkyl of up to 10 carbon atoms, or
   (c) a salt radical selected from alkali metals, alkaline earth metals and mono-, di-, or triethanolamine; when both M and M' are contained, there is the proviso that when either M or M' is an organic radical (b), the other of M and M' must be hydrogen or a salt radical (c);
X is an anion;
z is an integer from 0 to 2,
n is of a value necessary for charge balance;
R is a tertiary amine containing a total of from 6 to 60 carbon atoms.

6. Process as claimed in claim 5 wherein in the reaction is as follows:

$$\overset{+}{R}-Y-O-\underset{O^-}{\overset{\overset{O}{\|}}{P}}-OM \quad (II)$$

$$(2) \quad -Hal \uparrow$$

$$R + Hal-Y-O-\underset{OH}{\overset{\overset{O}{\|}}{P}}-OM \quad (IIa)$$

wherein the radicals are defined as before.

7. Process as claimed in claim 5 wherein the reaction is as follows:

$$\left[\overset{+}{R}-Y-O-\underset{OM'}{\overset{\overset{O}{\|}}{P}}-OM\right]^+ X^- \quad (III)$$

$$(3) \quad -Hal \uparrow$$

$$R + Hal-Y-O-\underset{OM'}{\overset{\overset{O}{\|}}{P}}-OM \quad (IIIa)$$

wherein the radicals are defined as before.

8. Process as claimed in claim 5 wherein the reaction is as follows:

$$\left[\overset{+}{R}-Y-O-\underset{O^-}{\overset{\overset{O}{\|}}{P}}-O-Y-R\right]^+ X^- \quad (IV)$$

$$(4) \quad \begin{array}{c}-Hal\\+X\end{array} \uparrow$$

$$2R + Hal-Y-O-\underset{OM}{\overset{\overset{O}{\|}}{P}}-O-Y-Hal \quad (IVa)$$

wherein the radicals are defined as before.

9. Process as claimed in claim 1 wherein said phosphate reactant is of the formula $$Cl-C-\underset{\phantom{O}}{\overset{OH}{\underset{|}{C}}}-C-O-\underset{OH}{\overset{\overset{O}{\|}}{P}}-ONa$$

or $$Cl-C-\underset{\phantom{O}}{\overset{OH}{\underset{|}{C}}}-C-O-\underset{OH}{\overset{\overset{O}{\|}}{P}}-OYCl$$

wherein
Y is hydroxypropyl
and wherein said amine reactant is of the formula $$R'-\overset{\overset{O}{\|}}{C}-NH-(CH_2)_n-N-(CH_3)_2$$

wherein
R' is alkyl of at least 5 carbon atoms or imidazolyl and n is 2 or 3.

10. Process as claimed in claim 9 wherein said phosphate reactant is $$Cl-C-\underset{\phantom{O}}{\overset{OH}{\underset{|}{C}}}-C-O-\underset{OH}{\overset{\overset{O}{\|}}{P}}-ONa$$

11. Process as claimed in claim 9 wherein said phosphate reactant is

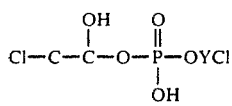

12. Process as claimed in claim 9 wherein in said amine reactant R' is alkyl.

13. Process as claimed in claim 9 wherein n is 2.

14. Process as claimed in claim 9 wherein n is 3.

15. Process as claimed in claim 9 wherein said reaction is carried out at a pH of 7 to 9 and at a temperature of 80° to 130° C.

16. Process as claimed in claim 1 wherein said amine reactant is of the formula

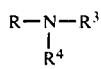

wherein
$R^3$ and $R^4$ are selected from alkyl and hydroxyalkyl of up to 6 carbon atoms; and
R is alkyl of 8 to 18 carbon atoms or imidazolyl.

17. Process as claimed in claim 16 wherein $R^3$ and $R^4$ are methyl.

18. Process as claimed in claim 1 wherein

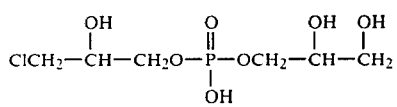

is reacted with 3-cocamidopropyl dimethylamine to produce the following phosphobetaine structure

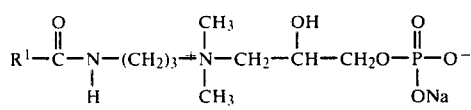

wherein $R^1$ is alkyl of 7 to 17 carbon atoms.

19. Process as claimed in claim 1 wherein

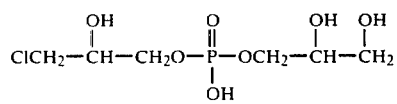

is reacted with 70/30 blend of 3-lauramidopropyl dimethylamine and 3-myristamidopropyl dimethylamine to produce the following phosphobetaine structure

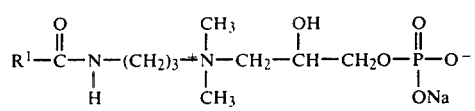

wherein $R^1$ is alkyl of 7 to 17 carbon atoms.

20. Process as claimed in claim 1 wherein

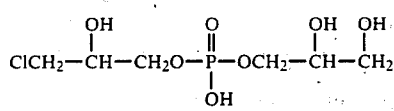

is reacted with 3-lauramidopropyl dimethylamine to produce the following phosphobetaine structure

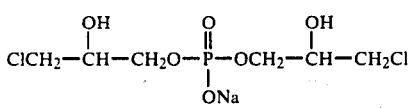

wherein $R^1$ is alkyl of 11 carbon atoms.

21. Process as claimed in claim 1 wherein

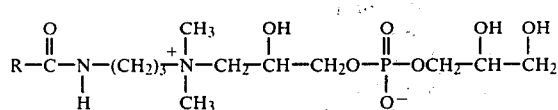

is reacted with 3-cocamidopropyl dimethylamine to produce the following phosphobetaine structure

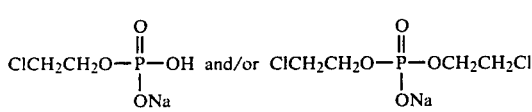

wherein R is alkyl of 7 to 17 carbon atoms.

22. Process as claimed in claim 1 wherein

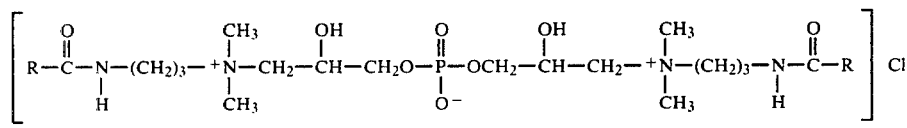

is reacted with 3-cocamidopropyl dimethylamine to produce the following phosphobetaine structure

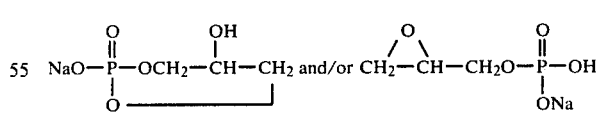

wherein R is alkyl of 7 to 17 carbon atoms.

23. Process as claimed in claim 1 wherein

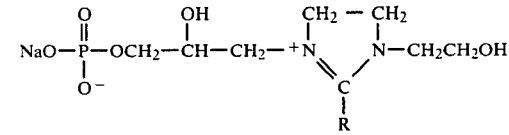

is reacted with 1-hydroxyethyl-2-alkyl-2-imidazoline to produce the following phosphobetaine structure wherein R is alkyl of 7 to 17 carbon atoms.

24. Process for the preparation of a 3-hydroxypropyl-phosphobetaine compound, which process comprises reacting an amine reactant with a cyclic hydroxypropylene containing phosphate ester reactant, wherein the amine reactant is selected from primary, secondary and tertiary amines having a total of from 6 to 60 carbon atoms therein.

25. Process as claimed in claim 24 wherein the reaction proceeds as follows:

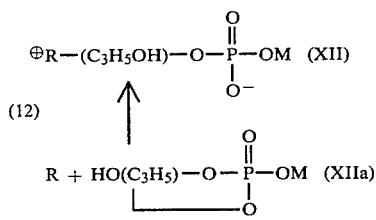

M and M', which may be the same or different, are
(a) hydrogen,
(b) an organic radical selected from alkyl or hydroxyalkyl of up to 6 carbon atoms, polyhydroxyalkyl of up to 10 carbon atoms, glyceryl, cycloalkyl of up to 6 carbon atoms, aryl or arylalkyl of up to 10 carbon atoms, or
(c) a salt radical selected from alkali metals, alkaline earth metals and mono-, di-, or triethanolamine; when both M and M' are contained, there is the proviso that when either M or M' is an organic radical (b), the other of M and M' must be hydrogen or a salt radical (c); and R is a tertiary amine reactant containing frm 6 to 60 carbon atoms.

26. Process as claimed in claim 24 wherein the reaction proceeds as follows:

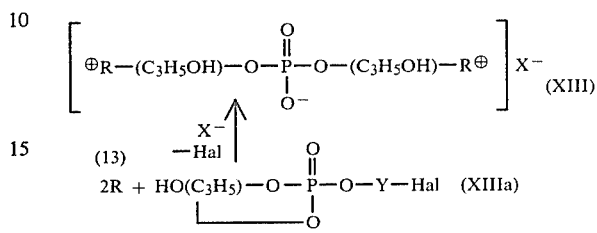

wherein
Y may be alkylene, optionally interrupted by up to 3 oxygen atoms, of up to 12 carbon atoms, which alkylene chain may optionally be substituted with lower alkyl, alkoxy, hydroxy or hydroxyalkyl of not more than 10 carbon atoms each;
Hal is halogen; and
R is a tertiary amine reactant containing from 6 to 60 carbon atoms.

* * * * *